(12) United States Patent
Blackledge et al.

(10) Patent No.: US 12,115,208 B2
(45) Date of Patent: Oct. 15, 2024

(54) SMALL-MOLECULE ADJUVANTS FOR ANTIBIOTICS TO ADDRESS ANTIBIOTIC RESISTANCE

(71) Applicant: HIGH POINT UNIVERSITY, High Point, NC (US)

(72) Inventors: Meghan Scobee Blackledge, Greensboro, NC (US); Patrick Andrew Vigueira, Winston-Salem, NC (US); Heather B. Miller, Pleasant Garden, NC (US)

(73) Assignee: High Point University, High Point, NC (US)

( * ) Notice: Subject to any disclaimer, the term of this patent is extended or adjusted under 35 U.S.C. 154(b) by 407 days.

(21) Appl. No.: 16/158,928

(22) Filed: Oct. 12, 2018

(65) Prior Publication Data

US 2019/0125825 A1 May 2, 2019

Related U.S. Application Data

(60) Provisional application No. 62/571,463, filed on Oct. 12, 2017.

(51) Int. Cl.
*A61K 38/14* (2006.01)
*A61K 31/335* (2006.01)
*A61K 31/553* (2006.01)
*A61P 31/04* (2006.01)

(52) U.S. Cl.
CPC ............ *A61K 38/14* (2013.01); *A61K 31/335* (2013.01); *A61K 31/553* (2013.01); *A61P 31/04* (2018.01)

(58) Field of Classification Search
CPC .... A61K 38/14; A61K 31/553; A61K 31/335; A61P 31/04
See application file for complete search history.

(56) References Cited

U.S. PATENT DOCUMENTS

| | | | | |
|---|---|---|---|---|
| 2002/0061281 A1* | 5/2002 | Osbakken | ............... | A61P 43/00 424/43 |
| 2007/0190160 A1* | 8/2007 | Turos | ................... | A61K 9/5138 424/490 |
| 2007/0196434 A1* | 8/2007 | Alimi | ..................... | A61K 33/40 424/434 |
| 2011/0200657 A1* | 8/2011 | Baker | ...................... | A61P 33/02 424/405 |
| 2014/0309266 A1* | 10/2014 | Wu | ......................... | A61K 45/06 514/382 |
| 2019/0135751 A1* | 5/2019 | Wang | ....................... | A61P 35/00 |

OTHER PUBLICATIONS

Cederlund et al., "Antibacterial activities of non-antibiotic drugs", 1993, Journal of Antimicrobial Chemotherapy 32, 355-365 (Year: 1993).*

NIH/NLM PubChem Compound Summary for Loratadine (https://pubchem.ncbi.nlm.nih.gov/compound/3957).*
Anti-inflammatory properties of antihistamines: an update. G. M. Walsh Clin Exp All Rev 2005; 5:21-25.*
Braun et al., "Adjunct effect of loratadine in the treatment of acute sinusitis in patients with allergic rhinitis," Allergy 1997:52: 650-655. (Year: 1997).*
Lin et al., "Design, synthesis and biological activity evaluation of desloratadine analogues as H1 receptor antagonists," Bioorganic & Medicinal Chemistry 21 (2013) 4178-4185. (Year: 2013).*
Wang et al., "Efficient HPLC method development using structure-based databasesearch, physico-chemical prediction and chromatographic simulation," Journal of Pharmaceutical and Biomedical Analysis 104 (2015)49-54. (Year: 2015).*
Boudreau et al., "Phosphorylation of BlaR1 in Manifestation of Antibiotic Resistance in Methicillin-Resistant *Staphylococcus aureus* and Its Abrogation by Small Molecules," *ACS Infectious Diseases*, 2015, p. 454-459, vol. 1.
Cutrona et al, "From Antihistamine to Anti-Infective: Loratadine Inhibition of Regulatory PASTA Kinases in *Staphylococci* Reduces Biofilm Formation and Potentiates ß-Lactam Antibiotics and Vancomycin in Resistant Strains of *Staphylococcus aureus*," *ACS Infectious Diseases*, 2019, p. 1-14.
Gillard et al., "Tricyclic Amine Antidepressants Suppress ß-Lactam Resistance in Methicillin-Resistant *Staphylococcus aureus* (MRSA) by Repressing mRNA Levels of Key Resistance Genes," *Chem Biol Drug Des.*, 2018, p. 1822-1829, vol. 92.
Gotoh et al., "Two-Component Signal Transduction as Potential Drug Targets in Pathogenic Bacteria," *Current Opinion in Microbiology*, 2010, p. 232-239, vol. 13.
Harris et al., "Potent Small-Molecule Suppression of Oxacillin Resistance in Methicillin-Resistant *Staphylococcus aureus*," 2012, p. 11254-1127, vol. 51.
Kawada-Matsuo et al., "Three Distinct Two-Component Systems are Involved in Resistance to the Class I Bacteriocins, Nukacin ISK-1 and Nisin A, in *Staphylococcus aureaus*," *Plos One*, Jul. 2013, p. 1-10, vol. 8, Issue 7.
Nguyen, et al., "The Discovery of 2-Aminobenzimidaloles That Sensitize Mycobacterium Smegmatis and M. Tuberculosis to ß-Lactam Antibiotics in a Pattern Distinct from ß-Lactamase Inhibitors," *Angewandte Chemie*, 2017, p. 3940-3944, vol. 56.
O'Callaghan et al., "Novel Method for Detection of ß-Lactamases by Using a Chromogenic Cephalosporin Substrate," *Antimicrobial Agents and Chemotherapy*, Apr. 1972, p. 283-288, vol. 1, No. 4.
Richards et al., "Controlling Bacterial Biofilms," *ChemBioChem*, 2009, p. 2287-2294, vol. 10.
Rogers et al., "Synergistic Effects Between Conventional Antibiotics and 2-Aminoimidazole-Derived Antibiofim Agents," *Antimicrobial Agents and Chemotherapy*, May 2010, p. 2112-2118, vol. 54, No. 5.

(Continued)

*Primary Examiner* — Aradhana Sasan
(74) *Attorney, Agent, or Firm* — Womble Bond Dickinson (US) LLP

(57) ABSTRACT

Methods for treating a bacterial infection and for suppressing antibiotic resistance in a patient are described herein. Certain such methods generally involve administering an antibiotic and an adjuvant compound to a patient with a bacterial infection caused by *Staphylococcus aureus*, wherein the adjuvant compound comprises a fused tricyclic ring system with at least one halogen substituent. Compositions and kits containing such components are also described.

20 Claims, 11 Drawing Sheets

(56) References Cited

OTHER PUBLICATIONS

Staude et al., "Investigation of Signal Transduction Routes Within the Sensor/Transducer Protein BlaR1 of *Staphylococcus aureus*," *Biochemistry*, Mar. 3, 2015, p. 1600-1610, vol. 54, No. 8.

Thumanu et al., "Discrete Steps in Sensing of ß-lactam Antibiotics by the BlaR1 Protein of the Methicillin-Resistant *Staphylococcus aureus* Bacterium," *PNAS*, Jul. 11, 2006, p. 10630-10635, vol. 103, No. 28.

Villegas-Estrada, et al., "Co-Opting the Cell Wall in Fighting Methicillin-Resistant *Staphylococcus aureus*: Potent Inhibition of PBP 2a by Two Anti-MRSA B-Lactam Antibiotics," *J. Am Chem Soc.*, Jul. 23, 2008, p. 9212-9213, vol. 130, No. 29.

Walsh, "Where will New Antibiotics Come From," *Nature Reviews Microbiology*, Oct. 2003, p. 65-70, vol. 1.

Wilson et al., "Resensitization of Methicillin-Resistant *Staphylococcus aureus* by Amoxapine, an FDA-Approved Antidepressant," *Heliyon*, Jan. 12, 2018, p. 1-11, vol. 4, No. 1.

Worthington et al., "Overcoming Resistance to ß-Lactam Antibiotics," *J. Org. Chem.*, 2013, p. 4207-4213, vol. 78.

Worthington, et al., "Small-Molecule Inhibition of Bacterial Two-Component Systems to Combat Antibiotic Resistance and Virulence," *Future Med. Chem.*, 2013, p. 1265-1284, vol. 5, No. 11.

Worthington, et al., "Combination Approaches to Combat Multi-Drug Resistant Bacteria," *Trends Biotechnol.*, Mar. 2013, p. 177-184, vol. 31, No. 3.

Wright, "Antibiotic Adjuvants: Rescuing Antibiotics from Resistance," *Trends in Microbiology*, Nov. 2016, p. 862-871, vol. 24, No. 11.

Conference Abstract Blackledge, et al. "Guided Inquiry and Drug Discovery: A Semester-Long Laboratory Sequence for Advanced Undergraduates," *American Chemical Society 253$^{rd}$ National Meeting*, San Francisco, CA, Apr. 4, 2017.

Poster Presentation Cutrona, et al., Halogenated dibenzoxazepines: Optimizing Antibiotic Adjuvant Activity, Jul. 2017.

Poster Presentation Cutrona et al., "Design and Synthesis of a Halogenated Dibenzoxazepine Library to Probe Antibiotic Adjuvant Activity," Jun. 2018.

Poster Presentation Gillard, et al."Investigation of FDA-Approved Small Molecules as Modulators of Virulence in Methicillin-Resistant *Staphylococcus aureus* (MRSA)," Apr. 2-3, 2017.

Poster Presentation Ulrich, et al., "Small Molecule Modulation of Virulence Behaviors in *Staphylococcus epidermidis*," Oct. 2017.

Poster Presentation Ulrich, et al., "Investigation of the Phenanthroline Scaffold as a Modulator of Virulence Behaviors in Methicillin-Resistant *Staphylococcus aureus* (MRSA) and *Staphylococcus epdermidis*," May 2018.

Student Poster Presentation Abstract; Regional and National Meetings: Cutrona, N.*, Gillard, K.* , Blackledge, M.S. "Design and synthesis of a halogenated dibenzoxazepine library to probe antibiotic adjuvant activity." 255$^{th}$ ACS National Meeting, New Orleans, LA, United States, Mar. 19, 2018.

Student Poster Presentation Abstract; Regional and National Meetings: Cutrona, N.*, Gillard, K.*, Blackledge, M.S. "Halogenated dibenzoxazepines: Optimizing antibiotic adjuvant activity." 69$^{th}$ Southeastern Regional Meeting of the American Chemical Society, Charlotte, NC, Nov. 8, 2017.

Student Poster Presentation Abstract; Regional and National Meetings: Gillard, K.*, Wilson, T.*, Vigueira, P., Sarkar, A., Blackledge, M.S. "Investigation of FDA-approved small molecules as modulators of virulence in methicillin-resistant *Staphylococcus aureus* (MRSA)." 253$^{rd}$ ACS National Meeting, San Francisco, CA, United States, Apr. 1-6, 2017. (Sci-Mix).

Student Poster Presentation Abstract; Regional and National Meetings: Nguyen, L.*, Blackledge, M.S. "Effects of FDA-approved compounds on biofilm formation and antibiotic sensitivity in *Staphylococcus haemolyticus*" 253$^{nd}$ ACS National Meeting, San Francisco, CA, United States, Apr. 1-6, 2017.

Student Poster Presentation Abstract; Regional and National Meetings: Ulrich, R.*, Behrens, M.*, Blackledge, M.S. "Small molecule modulation of virulence behaviors in *Staphylococcus epidermidis*." 253$^{rd}$ ACS National Meeting, San Francisco, CA, United States, Apr. 1-6, 2017.

Student Poster Presentation Abstract; At High Point University: Cutrona, N.*, Blackledge, M.S. "Design and synthesis of a halogenated dibenzoxazepine library to probe antibiotic adjuvant activity." HighPURCS, High Point, NC, Apr. 10, 2018.

Student Poster Presentation Abstract; At High Point University: Gillard, K.*, Wilson, T.*, Vigueira, P., Sarkar, A., Blackledge, M.S. "Investigation of FDA-approved small molecules as modulators of virulence in methicillin-resistant *Staphylococcus aureus* (MRSA)." HighPURCS, High Point, NC, Apr. 20, 2017.

Student Poster Presentation Abstract; At High Point University: Hendrix, M.*, Seemann, M.*, Gillard, K.*, Marshall, J.*, O'Brien, J.*, Wommack, A., Blackledge, M.S. "Evaluation of a diverse compound library as MRSA virulence modulators." HighPURCS, High Point, NC, Apr. 10, 2018.

Student Poster Presentation Abstract; At High Point University: Nguyen, L.*, Blackledge, M.S. "Effects of FDA-approved compounds on biofilm formation and antibiotic sensitivity in *Staphylococcus haemolyticus*" HighPURCS, High Point, NC, Apr. 20, 2017.

Student Poster Presentation Abstract; At High Point University: Ulrich, R.*, Behrens, M.*, Blackledge, M.S. "Small molecule modulation of virulence behaviors in *Staphylococcus epidermidis*." HighPURCS, High Point, NC, Apr. 20, 2017.

Student Poster Presentation Abstract; At High Point University: Ulrich, R.*, Nguyen, L.*, Baker, N.*, Blackledge, M.S. Probing the structure-activity relationship of *Escherichia coli* extracellular death factor. HighPURCS, High Point, NC, Apr. 13, 2016.

* cited by examiner

SMALL-MOLECULE ADJUVANTS FOR ANTIBIOTICS TO ADDRESS ANTIBIOTIC RESISTANCE

FIELD OF THE INVENTION

The present application is directed to methods and compositions for inhibiting bacterial biofilms and/or modifying antibiotic efficacy against bacterial infection and, in particular, to methods and compositions for treating infections caused by antibiotic-resistant and/or biofilm-forming bacteria.

BACKGROUND OF THE INVENTION

Each year, millions of Americans receive implanted medical devices (IMDs) ranging from artificial hip and knee implants to cardiac stents and urinary catheters. For any IMD, the most common post-surgical complication is bacterial infection. The devices are susceptible to contamination with bacteria both during the implantation process and in the course of daily use, and the bacteria can originate from healthcare workers or the patients themselves. Once bacteria have colonized an IMD, they can rapidly proliferate and form biofilms that help the bacteria evade the host immune response and antibiotic treatment. An estimated 12 million Americans are affected by biofilm-related infections each year, which carries an economic burden of nearly $6 billion. Furthermore, the overall infection burden on indwelling medical devices is expected to rise as the aging population grows and the use of IMDs increases.

Bacterial biofilms are three-dimensional communities of bacteria that are adhered to a surface and enclosed in an extracellular matrix. Bacteria in biofilms are up to 1,000 times more resistant to antibiotics than their planktonic counterparts and provide a reservoir for chronic infection. Currently, no FDA-approved therapies exist to prevent or disperse bacterial biofilms. The current treatment protocol for biofilm-infected IMDs is prolonged, high-dose antibiotic therapy and, in some cases, device removal. These treatments adversely impact the affected patients both financially, through lost wages and increased medical expenses, and in quality of life.

Nearly 80% of IMD infections are caused by one or more strains of staphylococci. Two strains in particular, *Staphylococcus aureus* and *Staphylococcus epidermidis*, account for two-thirds of all IMD infections. In addition to forming biofilms, *S. aureus* expresses a large number of toxins and virulence factors that create serious and pervasive infections. Although generally considered a less aggressive species, *S. epidermidis* has drawn increasing attention from the medical community as it forms robust and recalcitrant biofilms that can lead to bloodstream infections. Additionally, the prevalence of antibiotic-resistant isolates of both species, such as methicillin-resistant *S. aureus* (MRSA), vancomycin-resistant *S. aureus* (VRSA) and methicillin-resistant *S. epidermidis* (MRSE), have further reduced the available treatment arsenal.

In particular, methicillin-resistant *Staphylococcus aureus* (MRSA) is an opportunistic pathogen associated with soft tissue and systemic infections in humans. In 2005 alone, deaths from MRSA outnumbered those from AIDS, Parkinson's disease, emphysema, and homicide, combined. Resistant bacterial strains such as MRSA have developed genetically encoded resistance mechanisms to ensure their survival. The most common genotypic resistance mechanisms fall into one of three broad classes: (1) lowered intracellular antibiotic accumulation by decreased antibiotic uptake or increased efflux, (2) target modification to decrease the affinity of the target for the antibiotic, and (3) antibiotic inactivation via chemical modification or degradation of the antibiotic. In addition to the proteins directly involved in these resistance mechanisms, bacteria possess numerous proteins responsible for activating and regulating these mechanisms. These regulatory networks allow the bacteria to detect the presence of an antibiotic and initiate a signal cascade that results in either activation or upregulation of proteins necessary for resistance. Although rigorous healthcare initiatives have lowered infection rates by nearly 50% in the last decade, MRSA remains a prevalent and deadly pathogen in both community and healthcare settings. Hospital-acquired MRSA (HA-MRSA) infections traditionally exhibit multidrug-resistance and lead to increased length of hospitalization, higher treatment costs to patients, and higher mortality rates.

Antibiotics alone are inefficient at eradicating or fully preventing bacterial biofilms and can contribute to the enrichment of resistant strains of bacteria. Antibiotic resistance has become one of the most pressing health crises of the $21^{st}$ century, prompting officials in both the United States and around the world to call for action. While antibiotic-resistant infections were limited to healthcare and hospital settings for several decades, recently, community-acquired drug resistant infections have become increasingly common. Resistance has been observed to every known class of antibiotic, rendering our current arsenal of therapeutics increasingly useless.

Bacteria have evolved numerous methods for evading destruction by antibiotics. Some methods are phenotypic, such as formation of biofilms and persister cells, and provide innate protection from antibiotics. In the last 30 years, only two novel classes of antibiotics have been delivered to the market, linezolid and daptomycin. Bacteria developed resistance to these novel therapeutics almost as soon as they were deployed, despite their judicious use as drugs of last resort.

Therapeutics and methods for treating both antibiotic resistance and biofilm formation are thus urgently needed. However, given the slow rate of antibiotic discovery in the last thirty years and the ability of bacteria to develop resistance to new antimicrobials almost as soon as such antimicrobials are found, alternative approaches to combatting bacterial infections are needed to effectively stem the growing resistance crisis.

SUMMARY OF THE INVENTION

The present invention relates to methods and compositions for treating bacterial infection. The disclosed methods and compositions can, in some embodiments, provide for enhanced effectiveness of known antibiotics, especially β-lactam antibiotics (although not limited thereto). The disclosed methods and compositions can, in other embodiments, provide for treatment or prevention of biofilm formation.

In one aspect, the present disclosure provides a method for treating a bacterial infection in a patient caused by *Staphylococcus aureus*, comprising administering an antibiotic (e.g., a β-lactam antibiotic) and an adjuvant compound to the patient, wherein the adjuvant compound comprises a fused tricyclic ring system with at least one halogen substituent. Certain such adjuvants are depicted in Formula I, provided herein below. In one aspect, the present disclosure provides a method for treating a bacterial infection in a patient caused by *Staphylococcus aureus*, comprising administering an antibiotic (e.g., a β-lactam antibiotic) and an adjuvant compound to the patient, wherein the adjuvant compound comprises a halogen-substituted, carbazole-containing compound or a phenanthroline-containing compound as described herein (which may have, but does not require a halogen substituent for activity).

In another aspect, the disclosure provides a method for suppressing antibiotic resistance (e.g., β-lactam antibiotic resistance) in a patient with a bacterial infection caused by *Staphylococcus aureus*, comprising administering an antibiotic (e.g., a β-lactam antibiotic) and an adjuvant compound to the patient, wherein the adjuvant compound comprises a fused tricyclic ring system with at least one halogen substituent. Certain such adjuvants are depicted in Formula I. In another aspect, the disclosure provides a method for suppressing antibiotic resistance (e.g., β-lactam antibiotic resistance) in a patient with a bacterial infection caused by *Staphylococcus aureus*, comprising administering an antibiotic (e.g., a β-lactam antibiotic) and an adjuvant compound to the patient, wherein the adjuvant compound comprises a halogen-substituted, carbazole-containing compound or a phenanthroline-containing compound as described herein (which may have, but does not require a halogen substituent for activity).

In a further aspect, the disclosure provides a method for decreasing the minimum inhibitory concentration (MIC) of an antibiotic (e.g., a β-lactam antibiotic) needed to treat a patient with a bacterial infection caused by *Staphylococcus aureus*, comprising administering the antibiotic and an adjuvant compound to the patient, wherein the adjuvant compound comprises a fused tricyclic ring system with at least one halogen substituent (e.g., as shown below in Formula I). In a still further aspect, the disclosure provides a method for decreasing the minimum inhibitory concentration (MIC) of an antibiotic (e.g., a β-lactam antibiotic) needed to treat a patient with a bacterial infection caused by *Staphylococcus aureus*, comprising administering the antibiotic and an adjuvant compound to the patient, wherein the adjuvant compound comprises a halogen-substituted, carbazole-containing compound or a phenanthroline-containing compound as described herein (which may have, but does not require a halogen substituent for activity).

The adjuvant compound, in certain embodiments, is a compound according to the following formula:

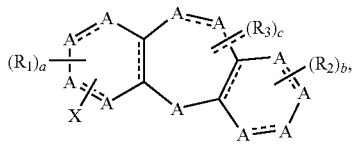

Formula I wherein:
each "A" is independently selected from C, N, O, and S;
X is a halogen substituent selected from Cl, F, Br, and I;
$R_1$, $R_2$, and $R_3$ are independently selected from halo (e.g., Cl, F, Br, and I); optionally substituted alkyl (e.g., C1-10 alkyl) (including halogenated alkyl (e.g., $CF_3$, 2-Br-ethyl, $CH_2F$, $CH_2Cl$, $CH_2CF_3$, or $CF_2CF_3$)); optionally substituted heteroalkyl, optionally substituted C2-4 alkenyl, optionally substituted C2-4 alkynyl; hydroxyl; amino; amido; carboxylate; carboxamido; carbamate; carbonate; urea; acetate; alkylamino; arylamino; acyl; C1-10 alkoxy; aryl; aralkyl, alkaryl, aryloxy; nitro; azido; cyano; thio; alkylthio; sulfonate; sulfide; sulfinyl; sulfo; sulfate; sulfoxide; sulfamide; sulfonamide; phosphonic acid; phosphate; and/or phosphonate;
a is an integer of 0 to 4;
b is an integer of 0 to 5;
c is an integer of 0 to 3; and
the dashed lines represent optional double bonds.

In certain embodiments, $R_3$ is an optionally substituted heteroalkyl group, e.g., including, but not limited to, an optionally substituted piperazine group. In certain embodiments, at least one of $R_1$ and $R_2$ is Cl.

In some embodiments, the adjuvant compound comprising the fused tricyclic system comprises a central ring fused to two side rings, wherein the at least one halogen substituent is on one of the side rings. The composition of the side rings can vary. In certain embodiments, one or both side rings are benzene rings. Exemplary fused tricyclic ring systems within the scope of Formula I include, but are not limited to, dibenzoxazepines, dibenzazepines, dibenzodiazepines, dibenzothiazepines, carbazoles, phananthrolines, and benzocycloheptapyridines. In certain specific embodiments, the adjuvant compound is selected from the group consisting of amoxapine, clozapine, loxapine, clothiaphine, loratadine, 3-chloro-10,11-dihydro-5H-dibenzo[b,f]-azepine and combinations thereof. Exemplary fused tricyclic ring systems outside the scope of Formula I, but which nonetheless are also encompassed by the present disclosure as adjuvants that can similarly potentiate antibiotics, include, but are not limited to, carbazoles and phenanthrolines. For example, in specific embodiments, the adjuvant comprises 3,6-dichlorocarbazole, 4-bromocarbazole, 5-methyl-1,10-phenanthroline, and/or 5-chloro-1,10-phenanthroline.

The antibiotic, in some embodiments, is a β-lactam antibiotic and, in certain specific embodiments, is a penicillin or a cephalosporin antibiotic. In some embodiments, the β-lactam antibiotic is selected from the group consisting of ampicillin, cefazolin, oxacillin, penicillin G, and combinations thereof. In other embodiments, the antibiotic comprises a glycopeptide antibiotic, e.g., vancomycin. In various embodiments, the *Staphylococcus aureus* is methicillin-resistant *Staphylococcus aureus* (MRSA) or vancomycin-resistant *Staphylococcus aureus* (VRSA).

The timing and specific method of administration of the antibiotic and adjuvant compound can vary. For example, in some embodiments, the antibiotic and the adjuvant compound are administered substantially simultaneously, and such administration can be such that the antibiotic and the adjuvant compound are administered in the same composition or such that the antibiotic and the adjuvant compound are administered in separate compositions. In some embodiments, the antibiotic and the adjuvant compound are administered at different times. The route of administration can similarly vary and, in certain embodiments, the antibiotic and the adjuvant compound are administered orally, parenterally, and/or topically.

Advantageously, in some embodiments, the antibiotic is administered in an amount less than its minimum inhibitory concentration when used alone. The patient is, in preferred embodiments, a human or animal.

The disclosure additionally provides, as a further aspect, a pharmaceutical composition comprising: an antibiotic (e.g., a β-lactam antibiotic); an adjuvant compound, wherein the adjuvant compound comprises a fused tricyclic ring system with at least one halogen substituent (e.g., falling within the scope of Formula I), and one or more pharmaceutically acceptable excipients. The disclosure further provides a pharmaceutical composition comprising: an antibiotic (e.g., a β-lactam antibiotic); an adjuvant compound, wherein the adjuvant compound comprises a fused tricyclic ring system comprising a phenanthroline or a halogen-substituted carbazole, and one or more pharmaceutically acceptable excipients.

In some such compositions, the antibiotic is present in an amount less than its minimum inhibitory concentration when used alone. The pharmaceutical composition can, in some embodiments, be in a form for oral administration, for parenteral administration, or for topical administration.

In a still further aspect, the disclosure provides a kit for the treatment of a patient with a bacterial infection caused by *Staphylococcus aureus* (e.g., methicillin-resistant *Staphylococcus aureus* (MRSA)) or vancomycin-resistant *Staphylococcus aureus* (VRSA)), comprising: a first pharmaceutical composition comprising an antibiotic (e.g., a β-lactam antibiotic) and one or more pharmaceutically acceptable excipients; and a second pharmaceutical composition comprising an adjuvant compound, wherein the adjuvant compound comprises a fused tricyclic ring system with at least one halogen substituent (e.g., a compound within the genus of Formula I). In one such embodiment, a kit is provided for the treatment of a patient with a bacterial infection caused by VRSA, wherein the adjuvant compound comprises loratidine. In some embodiments, the disclosure provides a kit for the treatment of a patient with a bacterial infection caused by MRSA or VRSA comprising: a first pharmaceutical composition comprising an antibiotic (e.g., a β-lactam antibiotic) and one or more pharmaceutically acceptable excipients; and a second pharmaceutical composition comprising an adjuvant compound, wherein the adjuvant compound comprises a fused tricyclic ring system comprising a carbazole with at least one halogen substituent or comprising phenanthroline.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise. Other aspects and advantages of the present invention will become apparent from the following.

BRIEF DESCRIPTION OF THE DRAWINGS

In order to provide an understanding of embodiments of the invention, reference is made to the appended drawings, which are not necessarily drawn to scale, and in which reference numerals refer to components of exemplary embodiments of the invention. The drawings are exemplary only, and should not be construed as limiting the invention.

DETAILED DESCRIPTION OF THE INVENTION

Figure 1:
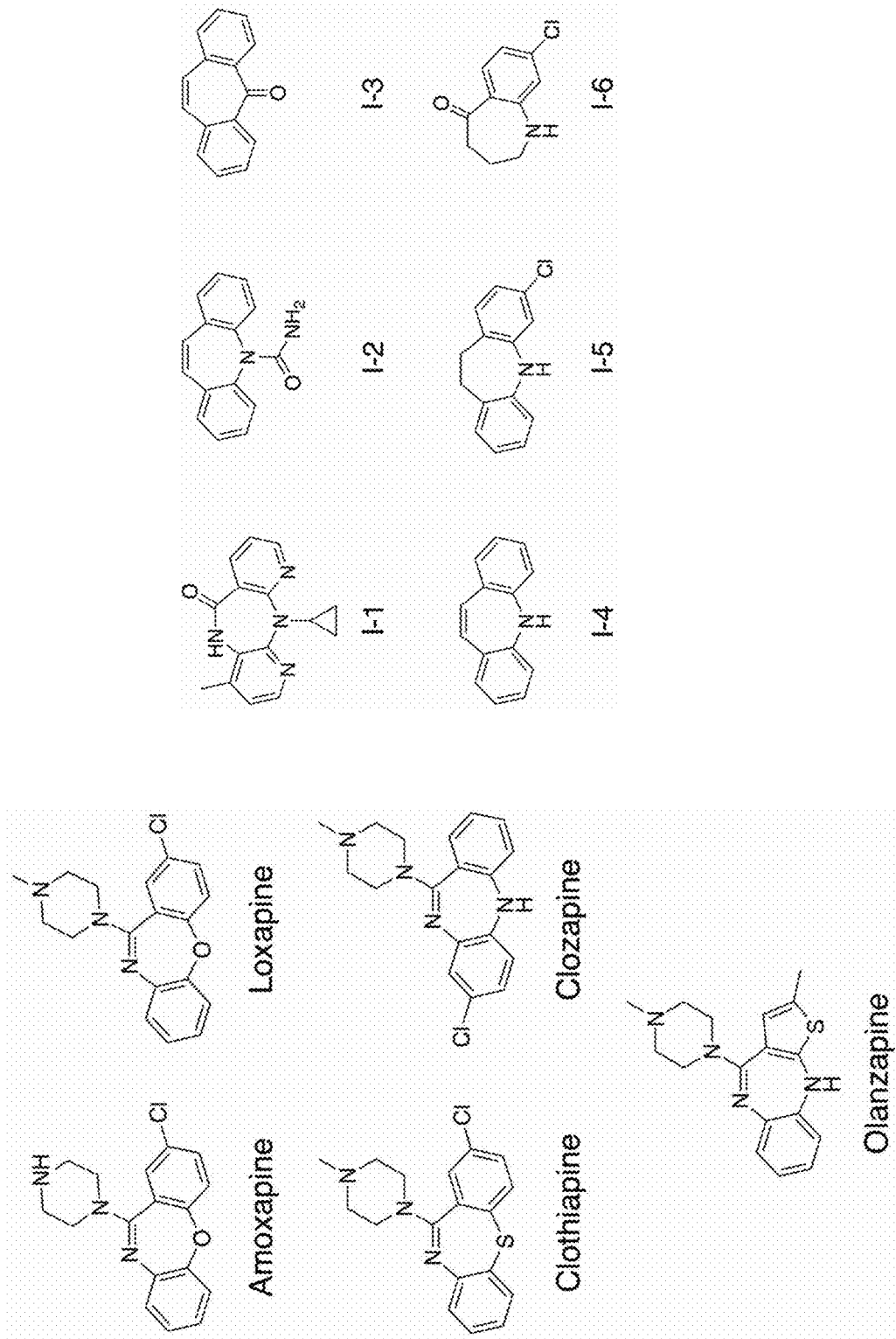
FIG. 1 shows various compounds evaluated for β-lactam antibiotic repotentiation in Example 1 provided herein.

The present invention will now be described more fully hereinafter with reference to the accompanying figures, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

The present disclosure provides methods and compositions to address bacterial biofilm formation and antibiotic resistance (e.g., including, but not limited to, resistance to certain β-lactam and/or aminoglycoside antibiotics). In general, the disclosure relates to the administration of one or more adjuvants with one or more antibiotic compounds to a patient, e.g., to treat a bacterial infection in the patient. The co-administration of the adjuvant(s) referenced herein with an antibiotic can serve, in various embodiments, to repotentiate (at least in part) the activity of the antibiotic against bacterial infection. The disclosure also relates to the administration of certain such adjuvants for biofilm inhibition.

Antibiotic adjuvants, more generally referred to in the present disclosure as "adjuvants" are understood to be potentiators of antibiotic activity. Adjuvants are active molecules that enhance the antimicrobial activity of one or more antibiotic compounds. In certain embodiments, adjuvants of the presently disclosed methods and compositions are not themselves antibiotic compounds and typically, are non-toxic compounds.

Adjuvant therapy is understood to be the use of a compound (adjuvant) to re-potentiate the toxic effects of an existing antibiotic. Because adjuvants alone are generally non-toxic, bacteria have very little selective pressure to develop resistance to these molecules, which increases their therapeutic lifetime. Advantageously, adjuvants can restore, at least to some extent, the therapeutic efficacy of existing antibiotics, e.g., those whose targets, mechanisms of action, and dosing regimens are generally well understood and which have been described in significant detail. Antibiotic adjuvants have already shown efficacy in clinical settings. Clavulanic acid, a compound with little antibiotic activity, has been successfully used in combination with amoxicillin as a broad-spectrum antibiotic treatment for over three decades.

According to the present disclosure, in particular embodiments, relevant adjuvants for use with an antibiotic as described herein are compounds containing a tricyclic ring system and, in particular, a tricyclic fused ring system. Further, certain particularly efficacious adjuvants according to the methods disclosed herein comprise a halo substituent (e.g., Cl, F, or Br) on one of the three rings (e.g., including, but not limited to, on one of the two rings adjacent to the central ring). Representative tricyclic ring systems are shown below and it is understood that any one or more (including one, two, or all three) of the three rings can be heterocyclic (containing one or more heteroatoms, e.g., N, O, or S) and/or substituted, e.g., with various substituents as referenced herein below. Each ring may be fully saturated or may comprise one or more double bonds. In some embodiments, one or more of the rings is aromatic. The sizes of the three rings can vary. In certain embodiments, the central ring of the fused ring system comprises a 7-membered ring. In certain embodiments, the side rings are each selected from a 5-membered ring and a six-membered ring.

For example, in some embodiments, the tricyclic ring system comprises an optionally substituted and optionally heterocyclic central ring with two benzene rings fused thereto. In some embodiments, the tricyclic ring system comprises an optionally substituted and optionally heterocyclic central ring with two rings fused thereto, wherein at least one of the two rings is a heterocyclic ring (e.g., pyridine, pyrimidine, thiophene, etc.). In some embodiments, the central ring is a 7-membered ring and the other two rings are independently selected from benzene, pyridine, and pyrimidine rings. In some embodiments, adjuvants encompassed within the present invention are not understood to have any significant antibacterial effects when administered alone. In some embodiments, adjuvants used according to the present disclosure are approved by the federal drug administration (FDA) for one or more purposes.

In certain embodiments, the adjuvant is represented by Formula I, below,

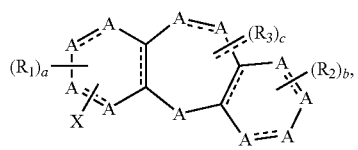

Formula I wherein:
  each "A" is independently selected from C, N, O, and S;
  X is a halogen substituent selected from Cl, F, Br, and I;
  $R_1$, $R_2$, and $R_3$ are independently selected from halo (e.g., Cl, F, Br, and I); optionally substituted alkyl (e.g., C1-10 alkyl) (including halogenated alkyl (e.g., $CF_3$, 2-Br-ethyl, $CH_2F$, $CH_2Cl$, $CH_2CF_3$, or $CF_2CF_3$)); optionally substituted heteroalkyl, optionally substituted C2-4 alkenyl, optionally substituted C2-4 alkynyl; hydroxyl; amino; amido; carboxylate; carboxamido; carbamate; carbonate; urea; acetate; alkylamino; arylamino; acyl; C1-10 alkoxy; aryl; aralkyl, alkaryl, aryloxy; nitro; azido; cyano; thio; alkylthio; sulfonate; sulfide; sulfinyl; sulfo; sulfate; sulfoxide; sulfamide; sulfonamide; phosphonic acid; phosphate; and/or phosphonate;
  a is an integer of 0 to 4;
  b is an integer of 0 to 5;
  c is an integer of 0 to 3; and
  the dashed lines represent optional double bonds.

One of skill in the art will recognize that, within this general structure, certain limitations exist, e.g., certain combinations of the above-referenced variables are not feasible within a compound. For example, double bonds are not possible at some positions due to the adjacent atoms and/or substituents thereon. In certain embodiments, the tricyclic ring system comprises at least one heteroatom (e.g., O, N, and/or S). In certain embodiments, $R_3$ is a heterocycloalkyl group. In certain embodiments, $R_3$ is an amine.

"Substituted" and "optionally substituted" refers to substituents that are, themselves, substituted or optionally substituted with one or more moieties selected from the group consisting of, for example, halo (e.g., Cl, F, Br, and I); alkyl (e.g., C1-10 alkyl), halogenated alkyl (e.g., $CF_3$, 2-Br-ethyl, $CH_2F$, $CH_2Cl$, $CH_2CF_3$, or $CF_2CF_3$); C2-4 alkenyl, C2-4 alkynyl; hydroxyl; amino; amido; carboxylate; carboxamido; carbamate; carbonate; urea; acetate; alkylamino; arylamino; acyl; C1-10 alkoxy; aryl; aralkyl, alkaryl, aryloxy; nitro; azido; cyano; thio; alkylthio; sulfonate; sulfide; sulfinyl; sulfo; sulfate; sulfoxide; sulfamide; sulfonamide; phosphonic acid; phosphate; and/or phosphonate.

The term "alkyl" as used herein means saturated straight, branched, or cyclic hydrocarbon groups (i.e., cycloalkyl groups). In particular embodiments, alkyl refers to groups comprising 1 to 10 carbon atoms ("C1-10 alkyl"). In further embodiments, alkyl refers to groups comprising 1 to 8 carbon atoms ("C1-8 alkyl"), 1 to 6 carbon atoms ("C1-6 alkyl"), or 1 to 4 carbon atoms ("C1-4 alkyl"). In other embodiments, alkyl refers to groups comprising 3-10 carbon atoms ("C3-10 alkyl"), 3-8 carbon atoms ("C3-8 alkyl"), or 3-6 carbon atoms ("C3-6 alkyl"). In specific embodiments, alkyl refers to methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl.

The term "cycloalkyl" means a non-aromatic, monocyclic or polycyclic ring comprising carbon and hydrogen atoms.

The term "heteroalkyl" as used herein means an alkyl group, having at least one atom within the chain which is not carbon. Preferred heteroatoms include sulfur, oxygen, and nitrogen. Heteroalkyls include cycloheteroalkyls, e.g., piperidines and piperazines.

The term "alkenyl" as used herein means alkyl moieties wherein at least one saturated C≡C bond is replaced by a double bond. In particular embodiments, alkenyl refers to groups comprising 2 to 10 carbon atoms ("C2-10 alkenyl"). In further embodiments, alkenyl refers to groups comprising 2 to 8 carbon atoms ("C2-8 alkenyl"), 2 to 6 carbon atoms ("C2-6 alkenyl"), or 2 to 4 carbon atoms ("C2-4 alkenyl"). In specific embodiments, alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl.

The term "alkynyl" as used herein means alkyl moieties wherein at least one saturated C≡C bond is replaced by a triple bond. In particular embodiments, alkynyl refers to groups comprising 2 to 10 carbon atoms ("C2-10 alkynyl"). In further embodiments, alkynyl refers to groups comprising 2 to 8 carbon atoms ("C2-8 alkynyl"), 2 to 6 carbon atoms ("C2-6 alkynyl"), or 2 to 4 carbon atoms ("C2-4 alkynyl"). In specific embodiments, alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl.

The term "aryl" as used herein means a stable monocyclic, bicyclic, or tricyclic carbon ring of up to 8 members in each ring, wherein at least one ring is aromatic as defined by the Hückel 4n+2 rule. Exemplary aryl groups according to the invention include phenyl, naphthyl, tetrahydronaphthyl, and biphenyl.

The term "alkoxy" as used herein means straight or branched chain alkyl groups linked by an oxygen atom (i.e., —O-alkyl), wherein alkyl is as described above. In particular embodiments, alkoxy refers to oxygen-linked groups comprising 1 to 10 carbon atoms ("C1-10 alkoxy"). In further embodiments, alkoxy refers to oxygen-linked groups comprising 1 to 8 carbon atoms ("C1-8 alkoxy"), 1 to 6 carbon atoms ("C1-6 alkoxy"), 1 to 4 carbon atoms ("C1-4 alkoxy") or 1 to 3 carbon atoms ("C1-3 alkoxy").

The term "amino" as used herein means a moiety represented by the structure $NR_4R_5$, and includes primary amines, and secondary and tertiary amines substituted by alkyl or aryl (i.e., alkylamino or arylamino, respectively). Thus, $R_4R_5$ may represent two hydrogen atoms, two alkyl moieties, two aryl moieties, one aryl moiety and one alkyl moiety, one hydrogen atom and one alkyl moiety, or one hydrogen atom and one aryl moiety.

The term "acyl" as used herein means a group formed by removing the hydroxyl group from a carboxylic acid, in which the non-carbonyl moiety of the group is selected from straight, branched, or cyclic alkyl or lower alkyl; alkoxyalkyl including methoxymethyl; aralkyl including benzyl; aryloxyalkyl such as phenoxymethyl; aryl including phenyl optionally substituted with halogen, C1-6 alkyl or C1-6 alkoxy; sulfonate esters such as alkyl or aralkyl sulphonyl including methanesulfonyl; mono-, di-, or triphosphate ester; trityl or monomethoxytrityl; substituted benzyl; trialkylsilyl such as dimethyl-t-butylsilyl or diphenylmethylsilyl.

The term "alkylthio" as used herein means a thio group with one or more alkyl substituents, where alkyl is defined as above.

The term "aralkyl" as used herein mean an aryl group as defined above linked to the molecule through an alkyl group as defined herein.

The term "alkaryl" as used herein means an alkyl group as defined above linked to the molecule through an aryl group as defined herein.

Alkyl(amino) is a moiety represented by the structure —$RNR_4R_5$ and includes an alkyl group as defined above attached to an amino group as defined above, wherein the moiety is attached to another portion of a molecule via the alkyl group.

Specific adjuvants useful in the methods disclosed herein that fall within the genus of Formula I above, include halo-substituted dibenzoxazepines, halo-substituted dibenzazepines, halo-substituted dibenzodiazepines, halo-substituted dibenzothiazepines, and halo-substituted benzocycloheptapyridines. The halogen substituent can vary and, for example, may be a chloro or fluoro substituent. The specific location of the halogen substituent on the tricyclic ring can vary. In some embodiments, the halogen substituent is on the central ring and in some embodiments, the halogen is on an outer ring. The compounds are not limited to having one halo substituent; in some embodiments, the compounds can comprise one, two, three, or more halo substituents. The compounds can, in some embodiments, have one or more additional substituents, such as those referenced herein above as $R_1$, $R_2$, and $R_3$ of Formula I.

Dibenzazepines generally contain two benzene rings fused to an azepine ring, e.g., as shown in the general structures below:

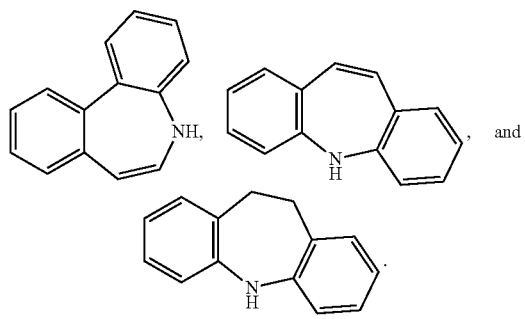

Dibenzodiazepines generally contain two benzene rings fused to a diazepine ring, e.g., as shown in the general structure below:

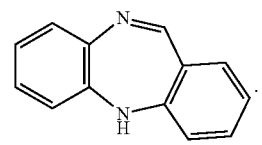

Dibenzoxazepines generally contain two benzene rings fused to a oxazepine ring, e.g., as shown in the general structure below:

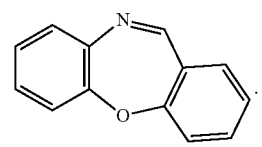 [SMILES: C1=Nc2ccccc2Oc2ccccc21]

Dibenzothiazepines generally contain two benzene rings fused to a thiazepine ring, e.g., as shown in the general structure below:

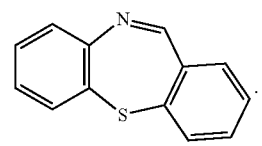

Benzocycloheptapyridines generally comprise a benzene ring and a pyridine ring fused to a cyclohepto ring, as shown in the general structure below:

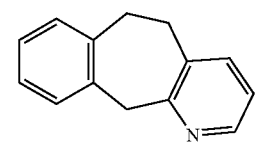 [SMILES: c1ccc2c(c1)CCc1cccnc1C2]

Certain specific exemplary adjuvants encompassed by the context of the present disclosure and falling within the above-referenced classes include, but are not limited to, 2-chloro-11-(1-piperazinyl)dibenz[b,f][1,4]oxazepine (amoxapine), 8-chloro-11-(4-methyl-1-piperazinyl)-5H-dibenzo[b,e][1,4]diazepine (clozapine), and 2-chloro-11-(4- methyl-1-piperazinyl)dibenz[b,f][1,4]oxazepine (loxapine), 8-chloro-6-(4-methylpiperazin-1-yl)benzo[b][1,4]benzothiazepine (clothiapine), 3-chloro-10,11-dihydro-5H-dibenzo[b,f]azepine, ethyl 4-(8-chloro-5,6-dihydrobenzo[1,2]cyclohepta[2,4-b]pyridin-11-ylidene)piperidine-1-carboxylate (loratadine), and combinations thereof.

Although the foregoing focuses on adjuvant compounds falling within the genus of Formula I, the disclosure is not limited thereto. In certain embodiments, fused tricyclic ring structure can vary. For example, the size of the central ring can vary from that depicted in Formula I, e.g., such that the central ring comprises five atoms or six atoms (rather than seven). Exemplary such compounds include, but are not limited to, carbazoles and phenanthrolines.

Carbazoles generally comprise two benzene rings fused to a five-membered N-containing ring, as shown in the general structure below:

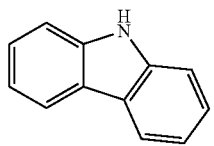 [SMILES: c1ccc2c(c1)[nH]c1ccccc12]

Phenanthrolines generally comprise two pyridine rings fused to a benzene ring, as shown in the general structure below:

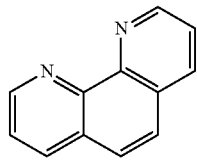 [SMILES: c1cnc2c(c1)ccc1cccnc12]

As noted above, any of these tricyclic fused ring systems can be heterocyclic and/or can be optionally substituted with any of the substituents referenced herein above.

It has interestingly been observed that, although a halide substituent provides enhanced activity in the context of various tested tricyclic fused ring systems (including compounds of Formula I and compounds comprising a carbazole), in certain embodiments, compounds without a halide substituent are effective. In particular, certain phenanthrolines without a halide substituent have demonstrated activity (see Example 5 below for further detail). Although not intending to be limited by theory, it is believed that activity of phenanthrolines as adjuvants is significantly affected by the position of one or more substituents present thereon. For example, in some embodiments, phenanthrolines with substituents at position 2 and/or 9 of may not exhibit significant repotentiation activity (which may be due to steric effects associated with binding). In some embodiments, phenanthrolines with electron donating groups at the 5 position exhibit enhanced repotentiation activity as compared to phenanthrolines with electron withdrawing groups at the 5 position. In some embodiments, phenanthrolines with non-ionizable, H-bond acceptors at one or more of the 4-7 positions on phenanthroline may exhibit improved repotentiation activity as compared to non-substituted analogues.

In certain particular embodiments, an adjuvant is employed comprising a carbazole or phenanthroline compound, wherein the compound is selected from 3,6-dichlorocarbazole, 4-bromocarbazole, 5-methyl-1,10-phenanthroline, 5-chloro-1,10-phenanthroline, and combinations thereof.

"Antibiotics" are understood to encompass compounds known in the art that have a deleterious effect on the viability, integrity, infectivity, or competence of an infectious agent. The term "antibiotic" is generally used synonymously with "antimicrobial." Certain antibiotics that are repotentiated in the presence of the adjuvants disclosed herein are antibiotics that are known for treatment of methicillin resistant *S. aureus* (MRSA) infections, methicillin sensitive *S. aureus* (MSSA) infections, and/or vancomycin-resistant *S. aureus* (VRSA) infections. Examples of antibiotics relevant in the context of the present disclosure include β-lactam antibiotics, β-lactamase inhibitors, aminoglycosides, aminocyclitols, quinolones, tetracyclines, macrolides, lincosamides, glycopeptides, lipopeptides, polypeptides, sulfonamides, trimethoprim, chloramphenicol, isoniazid, nitroimidazoles, rifampicins, nitrofurans, methenamine, and mupirocin. In particular preferred embodiments, the antibiotic comprises a β-lactam antibiotic and, in more particular preferred embodiments, the β-lactam antibiotic is a cephalosporin (e.g., including, but not limited to, cefazolin). "Antibiotics," in some embodiments, includes glycopeptide antibiotics. This antibiotic class includes, but is not limited to vancomycin, teicoplanin, oritavancin, telavancin, and dalbavancin.

The present invention relates, in some embodiments, specifically to the use of an adjuvant with a β-lactam antibiotic, which is the most commonly used class of antibiotic compounds (although, as referenced above, the disclosure is not limited thereto). The repotentiation of β-lactam antibiotics is particularly advantageous, due to the range of known antibiotics in this class, the significant characterization that has been conducted on various antibiotics in this class, and their efficacy with respect to treating a range of bacterial infections. β-lactam antibiotics generally comprise a β-lactam ring and include penams, carbapenams, oxapenams, penems, carbapenems, monobactams, cephems, carbacephems, and oxacephems.

Certain β-lactam antibiotics are penicillins, cephalosporins, monobactams, and carbapenem antibiotics. Specifically, β-lactam antibiotics include penicillin G, penicillin V, amoxycillin, ampicillin, apalcillin, aspoxicillin, azidocillin, azlocillin, aztreonam, benzylpenicillin, bacampicillin, carbenicillin, cloxacillin, cyclacillin, dicloxicillin, epicillin, flucloxacillin, lenampicillin, mecillinam, methicillin, mezlocillin, phenoxymethylpenicillin, piperacillin, pivampicillin, propicillin, sulbenicillin, talampicillin, and ticarcillin; cefaclor, cefadroxil, cefatrizine, cefclidine, cefamandole, cefazolin, cefbuperazone, cefcanel daloxate, cefdinir, cefepime, cefetamet pivoxil, cefixime, cefminox, cefminoxime, cefmetazole, cefonicid, cefoperazone, cefotaxime, cefotetan, cefotiam, cefotiam hexetil, cefoxitin, cefpimizole, cefpiramide, cefrirome, cefpodoxime proxetil, cefprozil, ceftazidime, ceftibuten, ceftizoxime, ceftriaxone, cefuroxime axetil, cefuroxime, cephacetrile, cephalexin, cephaloridine, cephalothin, cephamanadole nafate, cephapirin, cephoperazone, cefsulodin, cefuzonam, cephradine, loracarbef, DQ2556, ME1207, S1006, SCE2787, cloxacillin, dicloxacillin, flucloxacillin, methicillin, nafcillin, oxacillin, and temocillin.

Methods of Treatment

The disclosure provides methods for treating bacterial infections by administering an adjuvant as disclosed herein above and an antibiotic (e.g., a β-lactam antibiotic or vancomycin). In some embodiments, the bacterial infection is methicillin-resistant *Staphylococcus aureus* (MRSA). MRSA is generally resistant to methicillin, amoxicillin, penicillin, oxacillin, and many other common antibiotics. However, when antibiotics are administered in combination with an adjuvant as identified herein, the efficacy of the antibiotic may be at least partially restored. It is noted that the methods disclosed herein are described as being relevant, e.g., to treating patients with bacterial infections; however, it is to be understood that such methods are more broadly applicable, e.g., to patients being suspected of being, or at risk of being, or identified as being infected with undesired bacteria (e.g., MRSA, MSSA, or VRSA). It is noted that the application is largely directed to bacterial infections such as MRSA, MSSA, and VRSA; however, the methods, compositions, and kits described herein are not necessarily limited thereto; in some embodiments, for example, the methods, compositions, and kits are applicable for antibiotic potentiation in S. Epidermis (e.g., methicillin-resistant S. Epidermis).

By "administered in combination" is meant that both the antibiotic and the adjuvant are administered in a reasonably close time frame, such that both the antibiotic and the adjuvant are administered so as to be present in a patient at efficacious levels at the same time. As such, the bacteria at the site of the infection is advantageously exposed to efficacious levels of both the antibiotic and the adjuvant at the same time, regardless of how/when these two components were administered to the patient. The term "efficacious level/amount" means a concentration of the relevant compound, or a biologically active variant thereof, sufficient to elicit the desired therapeutic effect according to the methods of treatment described herein. In the context of antibiotic therapy, an efficacious amount is an amount that results in the amelioration of a bacterial infection.

In some embodiments, the antibiotic and the adjuvant are administered to a patient at the same time. For example, the antibiotic and the adjuvant can be contained within the same formulation or can be contained within separate compositions, administered substantially simultaneously. In other embodiments, the antibiotic and adjuvant can be administered at different times. For example, the antibiotic may be administered first, in the absence of the adjuvant and, subsequently, the adjuvant may be administered or the adjuvant may be administered first, in the absence of the antibiotic and, subsequently, the antibiotic may be administered. In such embodiments, the two components are administered within a close enough time period that the effect of the first component has not been lost at the time of administration of the second component.

Administering the antibiotic and the adjuvant according to the disclosed methods can be done orally, parenterally (including intravenously, intramuscularly, subcutaneously, intradermally, and transdermally), topically (including dermally, buccally, and sublingually), and/or rectally. The most useful and/or beneficial mode of administration can vary, especially depending upon the condition of the recipient and on the location of the bacterial infection being treated. The methods disclosed herein can be used to treat both human and animal patients. For example, the methods can be relevant for animals including, but not limited to, domestic animals such as dogs, cats, horses, rabbits, cows, goats, pigs, chickens, turkey, sheep, goats, and the like.

Advantageously, the methods of the present disclosure are effective in treating patients with a bacterial infection, e.g., resulting from bacteria considered to be resistant to one or more antibiotics, e.g., one or more β-lactam antibiotics. Administration of the disclosed adjuvants can, in some embodiments, be described as restoring, at least in part, the efficacy of antibiotics against even antibiotic-resistant bacteria (e.g., MRSA or VRSA). Efficacy in this context is understood to be some compromise of the viability, integrity or competence of the undesired bacteria (e.g., MRSA) such that the infected patient rids, eliminates, or overcomes the infection. Administration of an antibiotic and an adjuvant as provided herein more effectively treats a patient than antibiotic therapy alone by compromising the integrity of the bacteria in such a manner that the bacteria are rendered either incompetent, noninfectious or non-viable more rapidly or more effectively than they would be using the antibiotic in the absence of the adjuvant.

In some embodiments, administration of an adjuvant as disclosed herein with an antibiotic significantly lowers the MIC of the antibiotic. For example, in some embodiments, the methods disclosed herein lower the MIC of a β-lactam antibiotic about 2-fold or more, about 3-fold or more, or about 4-fold or more. In certain embodiments, the methods lower the MIC of a β-lactam antibiotic about 8-fold or more, about 10-fold or more, about 15-fold or more, or even about 30-fold or more. Various embodiments can be described as providing about a 2-fold to about a 40-fold reduction in the MIC of a β-lactam antibiotic. As such, methods of treatment provided herein against various bacteria can be effective with decreased concentrations of antibiotic necessary to arrest bacterial growth.

Compositions

While it is possible for the antibiotic and adjuvant of the present invention to be administered in the raw chemical form (substantially simultaneously or sequentially), it is preferred for one or both of the compounds (more preferably, both compounds) to be delivered as a pharmaceutical formulation. Accordingly, there are provided by the present invention pharmaceutical compositions comprising both an antibiotic and an adjuvant as described herein. As such, the compositions of the present invention comprise one or more antibiotics (e.g., β-lactam antibiotics or aminoglycoside antibiotics) and one or more adjuvants, together with one or more pharmaceutically acceptable carriers therefore, and optionally, other therapeutic ingredients. In some embodiments, the disclosed compositions may comprise further active agents, in addition to the one or more β-lactam antibiotics and/or one or more adjuvants.

By "pharmaceutically acceptable carrier" is intended a carrier that is conventionally used in the art to facilitate the storage, administration, and/or the healing effect of the active ingredient(s) of the pharmaceutical composition. The carrier(s) must be pharmaceutically acceptable in the sense of being compatible with the other ingredients of the formulation and not unduly deleterious to the recipient thereof. A carrier may also reduce any undesirable side effects of the active ingredient(s). Such carriers are known in the art. See, Wang et al. (1980) *J. Parent. Drug Assn.* 34(6):452-462, herein incorporated by reference in its entirety.

Additional ingredients for use in the compositions of the present invention can include any pharmaceutical ingredient commonly deemed acceptable in the art, such as binders, fillers, lubricants, disintegrants, diluents, surfactants, stabilizers, preservatives, flavoring and coloring agents, and the like. The compositions may further include diluents, buffers, binders, disintegrants, thickeners, lubricants, preservatives (including antioxidants), flavoring agents, taste-masking agents, inorganic salts (e.g., sodium chloride), antimicrobial agents (e.g., benzalkonium chloride), sweeteners, antistatic agents, surfactants (e.g., polysorbates such as "TWEEN 20" and "TWEEN 80", and pluronics such as F68 and F88, available from BASF), sorbitan esters, lipids (e.g., phospholipids such as lecithin and other phosphatidylcholines, phosphatidylethanolamines, fatty acids and fatty esters, steroids (e.g., cholesterol)), and chelating agents (e.g., EDTA, zinc and other such suitable cations). Exemplary pharmaceutical excipients and/or additives suitable for use in the compositions according to the invention are listed in Remington: The Science & Practice of Pharmacy," 21$^{st}$ ed. Lippincott Williams & Wilkins (2006); in the Physician's Desk Reference, 64$^{th}$ ed., Thomson PDR (2010); and in Handbook of Pharmaceutical Excipients, 6$^{th}$ ed., Eds. Raymond C. Rowe et al., Pharmaceutical Press (2009), which are incorporated herein by reference.

Binders are generally used to facilitate cohesiveness of compositions and ensure the composition (e.g., tablet) remains intact after compression. Suitable binders include, but are not limited to: starch, polysaccharides, gelatin, polyethylene glycol, propylene glycol, waxes, and natural and synthetic gums. Acceptable fillers include silicon dioxide, titanium dioxide, alumina, talc, kaolin, powdered cellulose, and microcrystalline cellulose, as well as soluble materials, such as mannitol, urea, sucrose, lactose, dextrose, sodium chloride, and sorbitol. Lubricants are useful for facilitating product manufacture and include vegetable oils, glycerin, magnesium stearate, calcium stearate, and stearic acid. Disintegrants, which are useful for facilitating disintegration of the pharmaceutical composition, generally include starches, clays, celluoses, algins, gums, and cross-linked polymers. Diluents, which are generally included to provide bulk, may include dicalcium phosphate, calcium sulfate, lactose, cellulose, kaolin, mannitol, sodium chloride, dry starch, and powdered sugar. Surfactants suitable for use in the formulation according to the present invention may be anionic, cationic, amphoteric, or nonionic surface active agents. Stabilizers may be included in the formulations to inhibit or lessen reactions leading to decomposition of the active agent, such as oxidative reactions.

Compositions of the present invention may include short-term, rapid-onset, rapid-offset, controlled release, sustained release, delayed release, and pulsatile release formulations, providing the composition achieve the desired administration of the components as described herein. See *Remington's Pharmaceutical Sciences* (18$^{th}$ ed.; Mack Publishing Company, Eaton, Penn., 1990), herein incorporated by reference in its entirety.

Pharmaceutical compositions according to the present invention are suitable for various modes of delivery, including oral, parenteral (including intravenous, intramuscular, subcutaneous, intradermal, and transdermal), topical (including dermal, buccal, and sublingual), and rectal administration. The most useful and/or beneficial mode of administration can vary, especially depending upon the condition of the recipient and the specific location of the bacterial infection being treated.

The pharmaceutical compositions may be conveniently made available in a unit dosage form, whereby such compositions may be prepared by any of the methods generally known in the pharmaceutical arts. Generally speaking, such methods of preparation comprise combining (by various methods) a β-lactam antibiotic and/or an adjuvant with a suitable carrier and/or one or more pharmaceutical ingredients. The combination of the β-lactam antibiotic and/or adjuvant with the one or more carriers and/or additional pharmaceutical ingredients is then physically treated to present the formulation in a suitable form for delivery (e.g., shaping into a tablet or forming an aqueous suspension).

Pharmaceutical compositions according to the present invention suitable as oral dosage may take various forms, such as tablets, capsules, caplets, and wafers (including rapidly dissolving or effervescing), each containing a predetermined amount of β-lactam antibiotic and/or adjuvant. The formulations may also be in the form of a powder or granules, a solution or suspension in an aqueous or non-aqueous liquid, and as a liquid emulsion (oil-in-water and water-in-oil). The active agent may also be delivered as a bolus, electuary, or paste. It is generally understood that methods of preparations of the above dosage forms are generally known in the art, and any such method would be suitable for the preparation of the respective dosage forms for use in delivery of the compounds according to the present invention.

A tablet containing an antibiotic and/or adjuvant according to the present invention may be manufactured by any standard process readily known to one of skill in the art, such as, for example, by compression or molding, optionally with one or more carriers and/or accessory ingredients. The tablets may optionally be coated or scored and may be formulated so as to provide slow or controlled release of the antibiotic and/or adjuvant.

Solid dosage forms may be formulated so as to provide a delayed release of the active agent, such as by application of a coating. Delayed release coatings are known in the art, and dosage forms containing such may be prepared by any known suitable method. Such methods generally include that, after preparation of the solid dosage form (e.g., a tablet or caplet), a delayed release coating composition is applied. Application can be by methods, such as airless spraying, fluidized bed coating, use of a coating pan, or the like. Materials for use as a delayed release coating can be polymeric in nature, such as cellulosic material (e.g., cellulose butyrate phthalate, hydroxypropyl methylcellulose phthalate, and carboxymethyl ethylcellulose), and polymers and copolymers of acrylic acid, methacrylic acid, and esters thereof.

Solid dosage forms according to the present invention may also be sustained release (i.e., releasing the antibiotic and/or adjuvant over a prolonged period of time), and may or may not also be delayed release. Sustained release formulations are known in the art and are generally prepared by dispersing a drug within a matrix of a gradually degradable or hydrolyzable material, such as an insoluble plastic, a hydrophilic polymer, or a fatty compound. Alternatively, a solid dosage form may be coated with such a material.

Formulations for parenteral administration include aqueous and non-aqueous sterile injection solutions, which may further contain additional agents, such as anti-oxidants, buffers, bacteriostats, and solutes, which render the formulations isotonic with the blood of the intended recipient. The formulations may include aqueous and non-aqueous sterile suspensions, which contain suspending agents and thickening agents. Such formulations for patenteral administration may be presented in unit-dose or multi-dose containers, such as, for example, sealed ampoules and vials, and may be stores in a freeze-dried (lyophilized) condition requiring only the addition of the sterile liquid carrier, for example, water (for injection), immediately prior to use. Extemporaneous injection solutions and suspensions may be prepared from sterile powders, granules, and tablets of the kind previously described.

The antibiotic and/or adjuvant according to the present invention may also be administered transdermally, wherein the antibiotic and/or adjuvant is incorporated into a laminated structure (generally referred to as a "patch") that is adapted to remain in intimate contact with the epidermis of the recipient for a prolonged period of time. Typically, such patches are available as single layer "drug-in-adhesive" patches or as multi-layer patches where the active agent(s) are contained in a layer separate from the adhesive layer. Both types of patches also generally contain a backing layer and a liner that is removed prior to attachment to the skin of the recipient. Transdermal drug delivery patches may also be comprised of a reservoir underlying the backing layer that is separated from the skin of the recipient by a semi-permeable membrane and adhesive layer. In some embodiments, the antibiotic and adjuvant can be contained within the same patch, in the same layer or separate layers. Transdermal drug delivery may occur through passive diffusion or may be facilitated using electrotransport or iontophoresis.

Formulations for rectal delivery of the antibiotic and adjuvant of the present invention include rectal suppositories, creams, ointments, and liquids. Suppositories may be presented as the active agent(s) in combination with a carrier generally known in the art, such as polyethylene glycol. Such dosage forms may be designed to disintegrate rapidly or over an extended period of time, and the time to complete disintegration can range from a short time, such as about 10 minutes, to an extended period of time, such as about 6 hours.

The antibiotic and adjuvant may be formulated in compositions including those suitable for oral, buccal, rectal, topical, nasal, ophthalmic, or parenteral (including intraperitoneal, intravenous, subcutaneous, or intramuscular injection) administration. The compositions may conveniently be presented in unit dosage form and may be prepared by any of the methods well known in the art of pharmacy. All methods include the step of bringing the antibiotic and/or adjuvant into association with a carrier that constitutes one or more accessory ingredients. In general, the compositions are prepared by bringing the antibiotic and/or adjuvant into association with a liquid carrier to form a solution or a suspension, or alternatively, bringing a compound of the invention into association with formulation components suitable for forming a solid, optionally a particulate product, and then, if warranted, shaping the product into a desired delivery form. Solid formulations of the invention, when particulate, will typically comprise particles with sizes ranging from about 1 nanometer to about 500 microns. In general, for solid formulations intended for intravenous administration, particles will typically range from about 1 nm to about 10 microns in diameter.

The amount of the antibiotic and/or adjuvant in the formulation will vary depending the specific compound(s) selected, dosage form, target patient population, and other considerations, and will be readily determined by one skilled in the art. The amount of the antibiotic and/or adjuvant in the formulation will be that amount necessary to deliver a therapeutically effective amount of the compound to a patient in need thereof to achieve at least one of the therapeutic effects associated with the compounds of the invention. In practice, this will vary widely depending upon the particular compound, its activity, the severity of the condition to be treated, the patient population, the stability of the formulation, and the like. Compositions will generally contain anywhere from about 1% by weight to about 99% by weight of a component disclosed herein, typically from about 5% to about 70% by weight, and more typically from about 10% to about 50% by weight, and will also depend upon the relative amounts of excipients/additives contained in the composition. Advantageously, the amount of antibiotic may, in some embodiments, be less than typically employed for treatment of bacterial infections, due to the reductions in minimum inhibitory concentrations of antibiotic demonstrated in the presence of adjuvants as disclosed herein.

In some embodiments, the compositions as disclosed herein each comprise only one or more antibiotics or one or more adjuvants. In certain embodiments, the disclosure provides a kit, comprising both a pharmaceutical composition comprising one or more antibiotics and a pharmaceutical composition comprising one or one or more adjuvants. In some embodiments, a known formulation of an antibiotic with relatively low dosage is provided together with a known formulations of an adjuvant with relatively low dosage (where such adjuvant is commercially available for other indications). Advantageously, in other embodiments, pharmaceutical compositions are provided which contain both of the one or more antibiotics and one or more adjuvants as disclosed herein.

Furthermore, certain of the "adjuvants" referred to herein are effective in inhibiting biofilm formation resulting from various bacterial infections. Treatment with such "adjuvants" alone has been shown, in some embodiments, to inhibit biofilm formation, e.g., in S. Aureus. For example, in some embodiments, loratidine is used to inhibit biofilm formation in S. Aureus, e.g., MRSA and VRSA. Treatment with "adjuvants" alone has been shown, in some embodiments, to inhibit biofilm formation in other bacteria-containing environments, e.g., in S. Epidermis. For example, loratidine and several phenanthroline derivatives are used to inhibit biofilm formation in S. Epidermis.

EXPERIMENTAL

Materials and Methods

Minimum Inhibitory Concentration

Minimum inhibitory concentrations were determined using a standard serial broth microdilution method. See Jorgensen, J. H.; Turnidge, J. D. In *Manual of Clinical Microbiology, Eleventh Edition*; American Society of Microbiology, 2015, which is incorporated herein by reference in its entirety. Mid-log-phase cultures were diluted to a concentration of approximately $5\times10^5$ CFU/ml in cation-adjusted Mueller-Hinton broth (CAMHB). Wells 2-11 of a 96-well polyvinylchloride microtiter plate were inoculated with 100 µl of bacterial suspension. 100 µl of uninoculated CAMHB was added to well 12 to serve as a negative control. The top wells were inoculated with 200 µl of bacterial suspension with either antibiotics or compounds added. Serial dilutions were performed in wells 2-10, leaving well 11 to serve as the positive control. The microtiter plates were covered with Press-n-Seal and incubated at 37° C. for 18 hours without agitation. Plates were scored by visual detection of well turbidity. Minimum inhibitory concentrations were recorded as the lowest concentration of compound or antibiotic at which no visible bacterial growth was observed.

Antibiotic Repotentiation

Tested bacteria was grown overnight in CAMHB at 37° C. with shaking. The overnight culture was diluted into fresh CAMHB to a concentration of $5\times10^5$ CFU/ml. The cell suspension (3 mL) was aliquoted into sterile culture tubes and compound was added to the appropriate concentration (≤25% of the compound MIC). Wells 2-11 of a 96-well polyvinylchloride microtiter plate were inoculated with 100 µl of bacterial suspension with added compound. 100 µl of uninoculated CAMHB was added to well 12 to serve as a negative control. The top wells were inoculated with 200 µl of bacterial suspension with antibiotic added to the suspension of bacteria and compound. Serial dilutions were performed in wells 2-10, leaving well 11 to serve as the positive control. On the same plate, a standard microdilution MIC with the tested antibiotics and no added compound was also performed to compare the antibiotic MIC in the presence and absence of compound. The microtiter plates were covered with Glad Press-n-Seal and incubated at 37° C. for 18 hours without agitation. Plates were scored by visual detection of well turbidity. Minimum inhibitory concentrations (MIC) were recorded as the lowest concentration of compound or antibiotic at which no visible bacterial growth was observed. Fold reductions were calculated by dividing the MIC of the antibiotic without compound by the MIC of the antibiotic in the presence of compound.

Growth Curves.

MRSA was grown overnight in CAMHB at 37° C. with shaking. The overnight culture was diluted into fresh CAMHB to a concentration of $5 \times 10^5$ CFU/ml. The cell suspension (3 mL) was aliquoted into sterile culture tubes and compound was added to achieve the desired concentrations. An untreated aliquot served as the control. 200 µl of each suspension or of the untreated control was aliquoted into a flat-bottomed microtiter plate. The plate was maintained at 37° C. with shaking and absorbance readings (600 nm) were recorded every 30 minutes for 24 hours.

Nitrocefin Hydrolysis Assays

For whole cell nitrocefin assays, bacteria was cultured overnight in CAMHB at 37° C. with shaking. The overnight culture was subcultured 1:100 in fresh CAMHB and grown at 37° C. with shaking to mid-log phase ($OD_{600}$=0.4-0.6). The culture was adjusted to an $OD_{600}$ of 0.2 in fresh CAMHB. The suspension was aliquoted (2 ml) into sterile culture tubes and treated with compound and/or oxacillin or left untreated. These suspensions were incubated at 37° C. with shaking for thirty minutes. The suspensions were adjusted to an $OD_{600}$ of 0.132 in phosphate buffered saline (PBS, pH 7, 900 µl). A 100 µl of a stock solution of nitrocefin (500 mg/ml in PBS) was added to these suspensions and mixed. The nitrocefin-bacteria suspensions (100 µl) were added to the wells of a clear 96-well polystyrene microtiter plate. A 50 mg/ml solution of nitrocefin in PBS served as a blank. Using BioTek Synergy H1 microplate reader maintained at 37° C., the absorbance at 486 nm was recorded every 5 minutes for 2 hours.

For lysed cell assays, bacteria was cultured overnight in CAMHB at 37° C. with shaking. The overnight culture was subcultured 1:100 in fresh CAMHB and grown at 37° C. with shaking to mid-log phase ($OD_{600}$=0.4-0.6). The culture was adjusted to an $OD_{600}$ of 0.2 in fresh CAMHB. The suspension was aliquoted (2 ml) into sterile culture tubes and treated with compound and/or oxacillin or left untreated. These suspensions were incubated at 37° C. with shaking for thirty minutes. The suspensions were adjusted to an $OD_{600}$ of 0.132 in phosphate buffered saline (PBS, pH 7, 900 µl). Cultures were lysed by sonication. A 100 µl of a stock solution of nitrocefin (500 mg/ml in PBS) was added to these suspensions and mixed. The nitrocefin-bacteria suspensions (100 µl) were added to the wells of a clear 96-well polystyrene microtiter plate. A 50 mg/ml solution of nitrocefin in PBS served as a blank. Using a BioTek Synergy H1 microplate reader maintained at 37° C., the absorbance at 486 nm was recorded every 5 minutes for 2 hours.

RNA Purification

MRSA was cultured overnight in CAMHB at 37° C. with shaking. The overnight culture was subcultured 1:100 in fresh CAMHB and grown at 37° C. with shaking to $OD_{600}$=0.35. The culture was adjusted to an $OD_{600}$ of 0.2 in fresh CAMHB. The suspension was aliquoted (2 ml) into sterile culture tubes and treated with compound and/or oxacillin or left untreated. These suspensions were incubated at 37° C. with shaking for one hour. Triplicate cultures of each condition were briefly centrifuged and cell pellets were stored at −80° C. Pellets were resuspended in 100 uL of lyphostaphin (1 mg/mL) and incubated at room temperature for 10 minutes. Next, lysates were subjected to a Qiashredder column and RNA was purified with RNeasy columns according to the manufacturer's protocol (Qiagen). An on-column DNase step was also included. Total RNA was quantified and purity was assessed with a Nanodrop spectrophotometer (Thermo Scientific). RNA integrity was visualized by agarose gel electrophoresis using GelRed (Phenix) and a ChemiDoc MP (BioRad).

RT-qPCR.

200 ng of total RNA was reverse transcribed using random primers, according to the manufacturer's protocol (BioRad select cDNA synthesis kit). Minus reverse transcriptase controls were prepared for each sample. Next, duplicate qPCR reactions were performed for each cDNA template using SYBR green according to the manufacturer's protocol (BioRad SYBR Green Supermix). Primer sequences are found in Supporting Information. Those that the authors designed used NCBI Primer Blast to specify the annealing temperatures, length, location, and analyze specificity and secondary structure. All reactions were run on a StepOne thermal cycler (Applied Biosystems). Cycling parameters were as follows: 95° C. for 10 minutes, 40 cycles of 95° C. for 15 seconds followed by 60° C. for 1 minute. Specificity of each primer pair was assessed with melt curve analyses and agarose gel electrophoresis. The efficiency of each primer pair was calculated using results from calibration curves generated in Microsoft Excel. Contaminating genomic DNA levels were calculated using the comparative Ct method. Gene expression levels relative to 16S rRNA were calculated using a relative quantification model.[17] Statistical significance was determined by unpaired student's t tests. All calculations were performed using Microsoft Excel.

Biofilm Inhibition

A standard static crystal violet assay was used to quantify biofilm inhibition.[45] Cultures of S. aureus or S. epidermidis were grown overnight in TSBG (tryptic soy broth with 5% glucose) at 37° C. with shaking. These cultures were used to inoculate fresh TSBG to a calculated optical density of 0.01 at 600 nm ($OD_{600}$). The diluted culture was aliquoted (2 mL) into sterile culture tubes and compound solutions were added to bring the aliquots to desired compound concentrations. Untreated aliquots were used as a positive control and water served as a negative control. 100 µl of these suspensions were added to the wells of a 96-well polyvinylchloride microtiter plate. The microtiter plates were wrapped in Glad Press-n-seal and incubated at 37° C. under stationary conditions for 30 hours. After incubation, media was discarded and the plates were washed with water to remove non-adherent cells. Adherent biofilms were stained with 110 µl of crystal violet (0.1% in water) and incubated at room temperature for thirty minutes. The crystal violet staining solution was discarded and plates were washed with water to remove excess stain. The resulting stained biofilms were solubilized with 200 µL of 95% ethanol for 10 minutes. 125 µl of the ethanol solutions were transferred to a clear polystyrene microtiter plate for evaluation. Absorbance at 540 nm was recorded using a BioTek Synergy H1 microplate reader. The absorbance of the negative control lanes was subtracted from the experimental values to account for background staining. Percent inhibition was calculated by comparison of the absorbance values of control versus treated wells under identical conditions.

Biofilm Dispersion Assay.

Overnight cultures of *S. aureus* or *S. epidermidis* were subcultured to an $OD_{600}$ of 0.01 in tryptic soy broth supplemented with 0.5% glucose (TSBG). For USA300Δ/+stk1, TSBG was supplemented with 0.2% xylose to induce transcription of stk1. 100 μl of the culture was distributed into rows 2-11 of a 96-well polyvinylchloride plate. Rows 1 and 12 were filled with 100 μl of sterile water and served as the negative controls. Plates were covered with Glad Press-n-Seal and incubated at 37° C. under stationary conditions for either 48 hours (*S. aureus* 29213, 43300, USA100, USA300, USA300 mutants, and *S. epidermidis*) or 24 hours (*S. aureus* 880 and NRS63SH). After the incubation period, the media was discarded and the plates were washed with water to remove non-adherent cells. Media containing the desired concentrations of compound was prepared and 100 μl was added to the desired rows. Media alone was added as a positive control and sterile water was added as a negative control. The plates were sealed with Glad Press-n-Seal and incubated under stationary conditions for another 24 hours. The media was discarded and plates were washed with water to remove any non-adherent bacteria. 110 μl of an aqueous crystal violet solution (0.1%) was added to each well and allowed to rest at room temperature to stain any biomass. After 30 minutes, the crystal violet solution was discarded and the plates were washed with water. The stained biomass was dissolved in 95% ethanol (200 μl) for 30 minutes and 125 μl was transferred to the corresponding wells of a flat-bottomed polystyrene 96-well plate. The absorbance of each well was measured at 540 nm. The wells that contained only water were used as background and subtracted from wells containing cultures.

Biofilm dispersion was quantified by calculating the ratio of the absorbance of the treated wells as compared to the untreated wells. These values were plotted and fit to a curve to determine the $EC_{50}$.

Compound Synthesis (III-1 Through III-5)

Desloratadine (100 mg, 0.321 mmol) was dissolved in anhydrous DMF (5 ml). Freshly ground NaOH (19.25 mg, 0.385 mmol) was added and the reaction was stirred at room temperature for 30 minutes. The solution was cooled to 0° C. and alkyl halide (0.482 mmol) was added dropwise. The reaction was allowed to warm to room temperature overnight. The crude product was extracted with ethyl acetate (30 ml) and washed with water (3×100 ml). The combined organic layers were dried over sodium sulfate and concentrated in vacuo. Flash chromatography (silica gel, 5% MeOH in DCM) provided the desired compounds.

Characterization Data for Select Synthesized Compounds 11-(1-butylpiperidin-4-ylidene)-8-chloro-6,11-dihydro-5H-benzo[5,6]cyclohepta[1,2-b]pyridine (III-1): $^1$H NMR (400 MHz, Chloroform-d) δ 8.36 (dd, J=4.8, 1.7 Hz, 1H), 7.43-7.38 (m, 1H), 7.13 (dd, J=1.8, 0.9 Hz, 1H), 7.11-7.03 (m, 3H), 3.42-3.27 (m, 2H), 2.93-2.71 (m, 4H), 2.65-2.57 (m, 1H), 2.54-2.39 (m, 7H), 1.56 (tt, J=8.0, 6.3 Hz, 2H), 1.36-1.24 (m, 2H), 0.89 (t, J=7.3 Hz, 3H); $^{13}$C NMR (101 MHz, cdcl$_3$) δ 157.06, 146.59, 139.58, 137.57, 137.44, 133.42, 132.84, 130.46, 128.98, 126.06, 122.23, 77.37, 77.05, 76.73, 57.92, 54.51, 54.44, 31.66, 31.42, 29.94, 29.67, 28.15, 20.65, 13.88; HR-MS (ESI), calcd $C_{23}H_{27}ClN_2$: [M+H]+ m/z: 367.186, found: 367.191.

8-chloro-11-(1-pentylpiperidin-4-ylidene)-6,11-dihydro-5H-benzo[5,6]cyclohepta[1,2-b]pyridine (III-2): $^1$H NMR (400 MHz, Chloroform-d) δ 8.36 (dd, J=4.8, 1.6 Hz, 1H), 7.41 (ddd, J=7.7, 1.7, 0.7 Hz, 1H), 7.15 (d, J=2.0 Hz, 1H), 7.11-7.04 (m, 3H), 3.41-3.27 (m, 2H), 3.00-2.92 (m, 1H), 2.89 (dd, J=11.4, 5.9 Hz, 1H), 2.86-2.77 (m, 2H), 2.77-2.66 (m, 2H), 2.57 (td, J=12.0, 11.3, 5.5 Hz, 5H), 1.65 (dq, J=14.9, 7.5 Hz, 2H), 1.37-1.21 (m, 5H), 0.87 (t, J=6.9 Hz, 3H); $^{13}$C NMR (101 MHz, Chloroform-d) δ 156.75, 146.62, 139.65, 137.57, 137.45, 133.43, 132.99, 130.27, 129.01, 126.12, 122.33, 77.36, 77.04, 76.72, 57.92, 54.24, 54.18, 31.58, 31.44, 29.42, 29.11, 25.21, 22.35, 13.90. HR-MS (ESI), calcd $C_{24}H_{29}ClN_2$: [M+H]+ m/z: 381.202, found: 381.198.

8-chloro-11-(1-nonylpiperidin-4-ylidene)-6,11-dihydro-5H-benzo[5,6]cyclohepta[1,2-b]pyridine (III-3): $^1$H NMR (400 MHz, Chloroform-d) δ 8.35 (td, J=4.1, 3.4, 1.6 Hz, 1H), 7.42 (ddd, J=7.8, 3.4, 1.6 Hz, 1H), 7.16 (dt, J=3.1, 1.8 Hz, 1H), 7.14-7.02 (m, 3H), 3.41-3.25 (m, 2H), 3.09 (ddd, J=11.8, 8.2, 3.8 Hz, 1H), 3.04-2.88 (m, 3H), 2.79 (tdd, J=15.4, 8.4, 4.3 Hz, 5H), 2.67 (t, J=5.9 Hz, 3H), 1.75 (t, J=7.6 Hz, 2H), 1.35-1.16 (m, 12H), 0.85 (td, J=6.7, 3.3 Hz, 3H); $^{13}$C NMR (101 MHz, cdcl$_3$) δ 156.19, 146.63, 139.76, 137.81, 137.21, 133.48, 133.24, 129.94, 129.07, 126.22, 122.51, 77.35, 77.04, 76.72, 57.60, 53.86, 53.80, 31.76, 31.47, 31.45, 29.34, 29.14, 29.13, 27.09, 22.60, 14.06. HR-MS (ESI), calcd $C_{28}H_{37}ClN_2$: [M+H]+ m/z: 401.171, found: 401.189.

8-chloro-11-(1-(4-isopropylbenzyl)piperidin-4-ylidene)-6,11-dihydro-5H-benzo[5,6]cyclohepta[1,2-b]pyridine (III-5): $^1$H NMR (400 MHz, Chloroform-d) δ 8.37 (dd, J=4.8, 1.7 Hz, 1H), 7.43-7.38 (m, 1H), 7.24 (d, J=1.8 Hz, 1H), 7.23 (s, 1H), 7.16 (d, J=2.0 Hz, 1H), 7.15 (d, J=1.1 Hz, 2H), 7.13 (s, 1H), 7.10 (t, J=1.1 Hz, 2H), 7.06 (dd, J=7.6, 4.8 Hz, 1H), 3.53 (s, 2H), 3.43-3.30 (m, 3H), 2.82-2.70 (m, 3H), 2.55 (ddd, J=13.8, 9.6, 4.2 Hz, 1H), 2.46 (ddd, J=13.6, 9.3, 4.2 Hz, 1H), 2.41-2.29 (m, 3H), 1.22 (d, J=6.9 Hz, 6H); $^{13}$C NMR (101 MHz, Chloroform-d) δ 157.52, 147.92, 146.58, 139.51, 137.76, 137.23, 133.38, 132.80, 132.63, 130.75, 129.35, 128.93, 126.29, 125.96, 122.07, 62.38, 54.58, 54.50, 33.76, 31.79, 31.42, 30.63, 30.38, 23.99. HR-MS (ESI), calcd $C_{23}H_{27}ClN_2$: [M+H]+ m/z: 443.218, found: 443.219.

Example 1

Tricyclic amine antidepressants based on the amoxapine scaffold were studied to evaluate if they were capable of disarming MRSA resistance mechanisms and restoring the efficacy of β-lactam antibiotics. The minimum inhibitory concentration (MIC) of each compound against the studied *S. aureus* strains was determined (see Table 1) using a standard broth microdilution protocol. See Jorgensen, J. H.; Turnidge, J. D. In *Manual of Clinical Microbiology, Eleventh Edition*; American Society of Microbiology, 2015, which is incorporated herein by reference in its entirety. The compounds were then analyzed for antibiotic repotentiation activity. The minimum inhibitory concentration of oxacillin, a β-lactam antibiotic, against planktonic bacteria was determined in the presence and absence of these compounds was determined at concentrations of 75 μM and 150 μM (≤25% of the amoxapine MIC) using a standard broth microdilution protocol. See Jorgensen, J. H.; Turnidge, J. D. In *Manual of Clinical Microbiology, Eleventh Edition*; American Society of Microbiology, 2015, which is incorporated herein by reference in its entirety. Treatment with amoxapine lowered the MICs of the tested β-lactam antibiotics between 8- and 32-fold (see Table 3). Structurally related compounds loxapine and clozapine showed similar β-lactam repotentiation, indicating that these compounds possess a similarly active pharmacophore (see Table 2). Further studies with amoxapine in combination with other cell-wall active antibiotics such as β-lactams, cephalosporins, and aminoglycosides showed that amoxapine was capable of potentiating β-lactam and cephalosporin antibiotics in MRSA (see Table 3). Amoxapine was further evaluated in various *S. aureus* strains to determine if the observed antibiotic repotentiation activity was consistent across medically relevant strains of *S. aureus* (see Table 4). The tested strains included USA300, which is a common and particularly virulent strain of community-acquired MRSA. Amoxapine was able to potentiate oxacillin in USA300, indicating that these compounds possess adjuvant activity in numerous medically relevant strains of *S. aureus*.

TABLE 1

MIC of various tricyclic amines and dibenzoxazepines against various *S. aureus* strains

| Strain Name | MIC values (μM) | | | | |
|---|---|---|---|---|---|
| | Amoxapine | Loxapine | Clothiapine | Clozapine | Olanzapine |
| *S. aureus* ATCC 29213 | 600 | 600 | >150 | 1200 | 600 |
| *S. aureus** ATCC 43300 | 600 | 600 | >150 | 600 | 600 |
| *S. aureus** USA300 | 600 | 600 | >150 | 600 | 600 |

TABLE 2

MIC of oxacillin in combination with tricyclic amine antidepressants in *S. aureus* 43300 (MRSA)

| | +75 μM compound | | +150 μM compound | |
|---|---|---|---|---|
| Compound | MIC (μg/mL) | Fold Reduction | MIC (μg/mL) | Fold Reduction |
| — | 32 | — | 32 | — |
| Amoxapine | 8 | 4 | 2 | 16 |
| Loxapine | 32 | 1 | 8 | 4 |
| Clothiapine | 4 | 8 | —* | —* |
| Clozapine | 32 | 1 | 4 | 8 |
| Olanzapine | 32 | 1 | 32 | 1 |

*Clothiapine was not tested at 150 μM because it was not soluble at this concentration

TABLE 3

MIC of antibiotics in combination with amoxapine in *S. aureus* 43300 (MRSA)

| | | +Amoxapine (150 μM) | |
|---|---|---|---|
| Antibiotic | MIC (μg/mL) | MIC (μg/mL) | Fold Reduction |
| Oxacillin | 32 | 2 | 16 |
| Ampicillin | 32 | 4 | 8 |
| Penicillin | 16 | 1 | 16 |
| Cefazolin | 16 | 0.5 | 32 |
| Vancomycin | 2 | 2 | 1 |

TABLE 4

MIC of oxacillin alone and in combination with amoxapine

| | | +Amoxapine (150 μM) | | +Amoxapine (75 μM) | |
|---|---|---|---|---|---|
| *S. aureus* Strain | Oxacillin MIC (μg/mL) | Oxacillin MIC (μg/mL) | Fold Reduction | Oxacillin MIC (μg/mL) | Fold Reduction |
| ATCC 29213 | 0.25 | 0.125 | 2 | 0.25 | 1 |
| ATCC 43300* | 32 | 2 | 16 | 8 | 4 |
| USA 300* | 32 | 2 | 16 | 16 | 2 |

*denotes methicillin-resistant strain

Other FDA-approved and/or commercially available compounds with structural similarities to amoxapine were also evaluated for antibiotic potentiation (see Table 5). It was found that compounds with fused tricyclic rings and an aromatic chloride effectively potentiated β-lactam antibiotics (see Table 5 and FIG. 1).

TABLE 5

Re-potentiation of MRSA (ATCC 43300) to oxacillin with FDA-approved or commercially available compounds

| Compound | Compound Concentration (μM) | Oxacillin MIC (μg/mL) | Fold Reduction |
|---|---|---|---|
| — | — | 16 | — |
| I-1 | 50 | 16 | 1 |
| I-2 | 50 | 16 | 1 |
| I-3 | 50 | 16 | 1 |
| I-4 | 50 | 16 | 1 |
| I-5 | 50 | 1 | 16 |
| I-6 | 50 | 16 | 1 |

Figure 2:
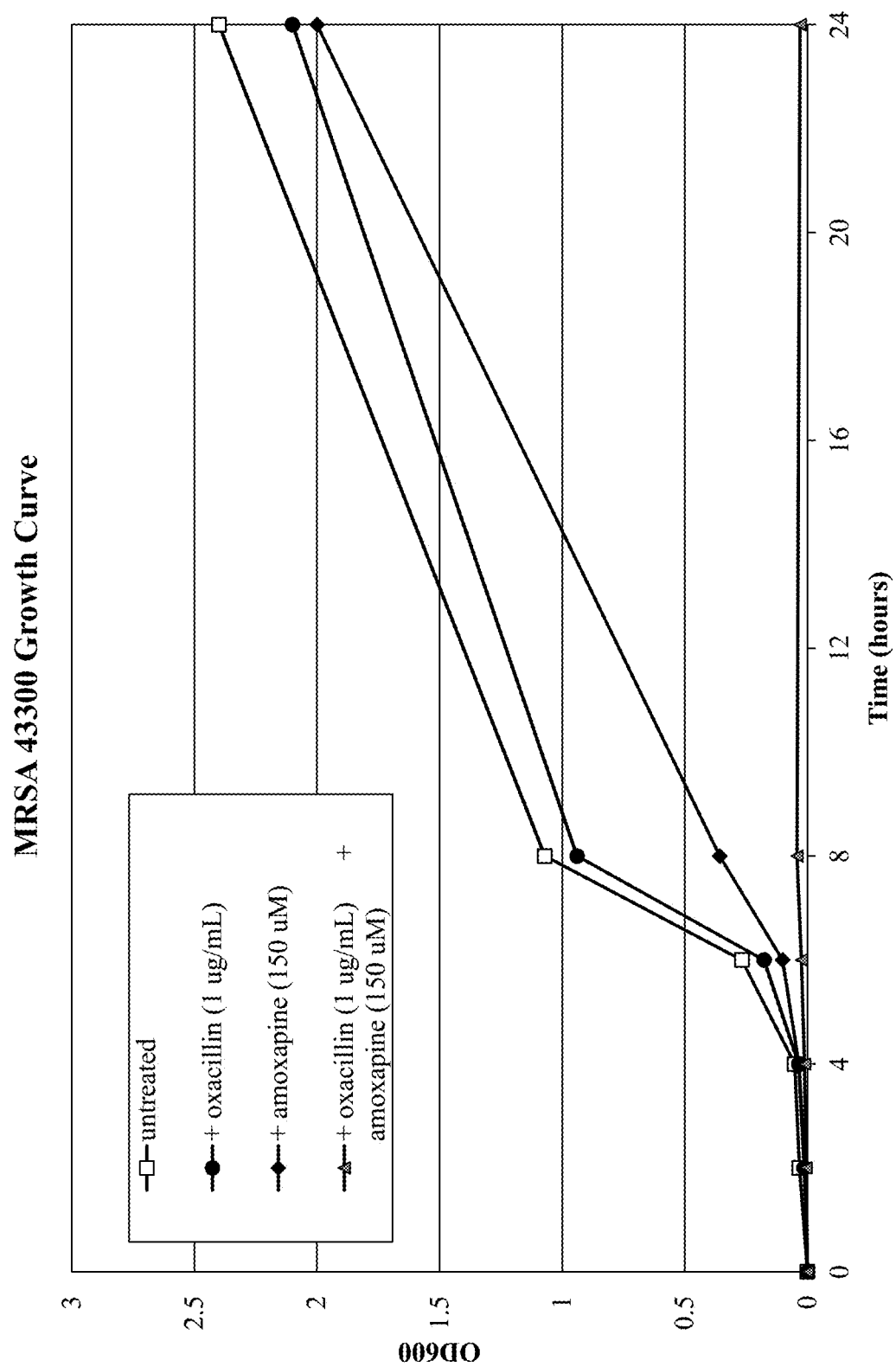
FIG. 2 is a growth curve of a MRSA bacterial strain, alone and in the presence of an antibiotic and/or an adjuvant.

It was clear from the repotentiation assays that simultaneous treatment of MRSA with β-lactam antibiotics and halogenated dibenzoxazepine derivatives dramatically reduced the concentration of antibiotic necessary to arrest bacterial growth. Using amoxapine and oxacillin as a representative adjuvant (e.g., dibenzoxazepine)/β-lactam combination, growth curves were made to observe the effects of combination therapy versus singular treatment with either β-lactam antibiotic or adjuvant over 24 hours. MRSA was grown in cation-adjusted Mueller-Hinton broth (CAMHB). MRSA cultures supplemented with oxacillin (1 μg/mL) in the presence and absence of amoxapine (150 μM) and amoxapine alone (150 μM) were grown concurrently with the untreated control. The optical density of the cultures at 600 nm was measured every 2 hours for 8 hours and again at 24 hours. See FIG. 2. As shown, treatment with oxacillin or amoxapine alone had a negligible effect on cell density after 24 hours. However, the combination of oxacillin and amoxapine showed potent inhibition of cell density throughout the course of the experiment.

Based on this understanding that amoxapine was indeed acting as an adjuvant to suppress β-lactam resistance in MRSA, studies were conducted seeking to characterize the mechanistic basis for this activity. Most bacteria develop β-lactam resistance either through the production of β-lactamases or through the production of an additional penicillin binding protein (PBP) to lower its affinity for the β-lactams; MRSA uses both strategies. In the presence of cell-wall modifying agents, MRSA induces expression of β-lactamase, controlled by the bla genes, and PBP2a, controlled by the mec genes. A nitrocefin hydrolysis assay was conducted according to known methods to determine whether amoxapine was acting as an inhibitor of β-lactamase using a nitrocefin hydrolysis assay. Nitrocefin is a chromogenic β-lactam with negligible antibiotic activity. Hydrolysis of nitrocefin produces an absorbance shift from 390 nm to 486 nm that can be measured and quantified spectrophotometrically. See O'Callaghan, C. H.; Morris, A.; Kirby, S. M.; Shingler, A. H. Novel method for detection of beta-lactamases by using a chromogenic cephalosporin substrate. *Antimicrob. Agents Chemother.* 1972, 1 (4), 283, which is incorporated herein by reference in its entirety. Nitrocefin hydrolysis has been used to measure β-lactamase activity in many β-lactamase producing bacteria, including MRSA.

Figures 3A, 3B:
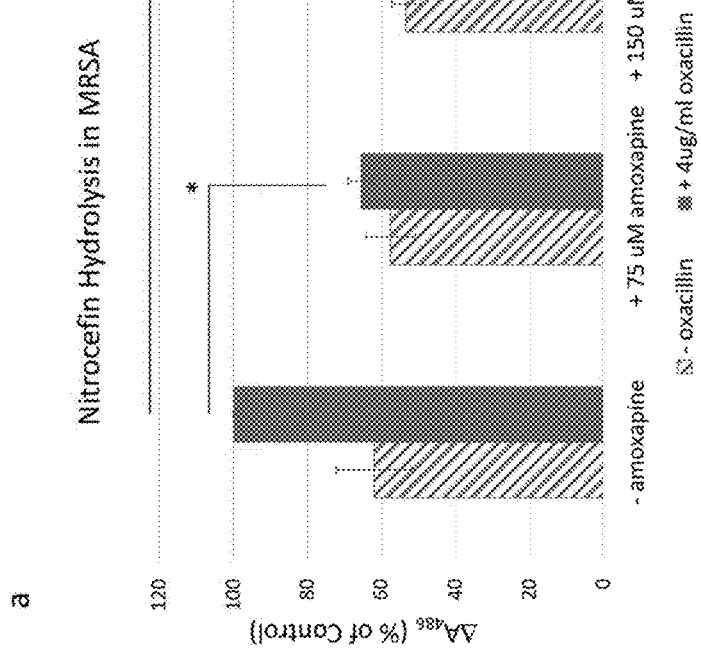
FIGS. 3A and 3B provide data with respect to the role of adjuvant amoxapine in β-lactam antibiotic repotentiation, in the form of MRSA (FIG. 3A) and MSSA (FIG. 3B) whole cell nitrocefin hydrolysis assays.
Figure 5:
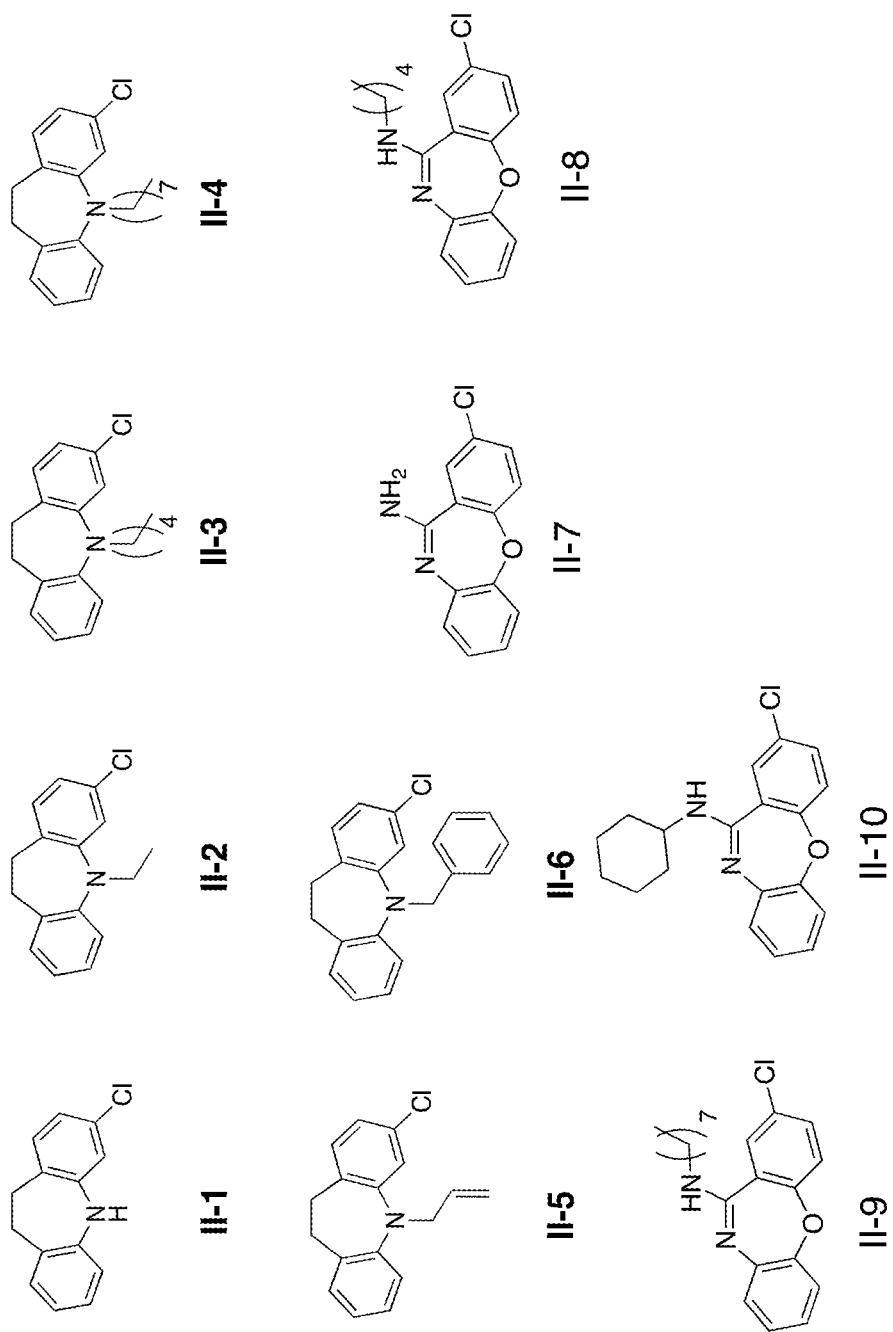
FIG. 5 shows various compounds evaluated for β-lactam antibiotic repotentiation in Example 2 provided herein.

Intact cells from MRSA strain 43300 (with and without induction with 4 mg/ml oxacillin) were evaluated for their ability to hydrolyze nitrocefin in the presence of amoxapine alone or in combination with oxacillin (See FIG. 3A). Absorbance at 486 nm was monitored for 2 hours. The change in absorbance at 486 nm is expressed as a percentage of the oxacillin-induced control. The mean of 3 independent biological replicates, each performed with 4 technical replicates, is shown in FIG. 5. Error bars represent standard deviation. * indicates p<0.05 versus the oxacillin only control. Panel (a) shows nitrocefin hydrolysis by MRSA ATCC 43300, panel (b) shows nitrocefin hydrolysis by MSSA ATCC 29213.

Treatment with oxacillin alone induced production of β-lactamase leading to increased levels of nitrocefin hydrolysis, as expected. In contrast, intact MRSA 43300 cells treated with a combination of amoxapine and oxacillin showed markedly less absorbance as compared to oxacillin alone. This indicated that amoxapine treatment was affecting β-lactamase activity, but it was not yet clear whether amoxapine was a β-lactamase inhibitor or was acting by some other mechanism.

To assess whether amoxapine was acting as an inhibitor of β-lactamase, a similar assay was performed on methicillin sensitive *S. aureus* (MSSA) strain 29213. MSSA 29213 produces endogenous β-lactamase and does not require induction with β-lactams for activity. Thus, it could be used to probe whether amoxapine alone was sufficient to inhibit β-lactamase. The known β-lactamase inhibitor sulbactam was used as a positive control. Again, all assays were run in triplicate and each data point represents the average of three data points. As seen in FIG. 3B, amoxapine treatment alone showed no effect on β-lactamase activity as compared to untreated cells. Treatment with oxacillin alone or in combination with amoxapine showed little effect on β-lactamase activity. Together, these data indicated that amoxapine does not directly inhibit β-lactamase activity nor does it appear to prevent β-lactamase export.

Figures 4A, 4B:
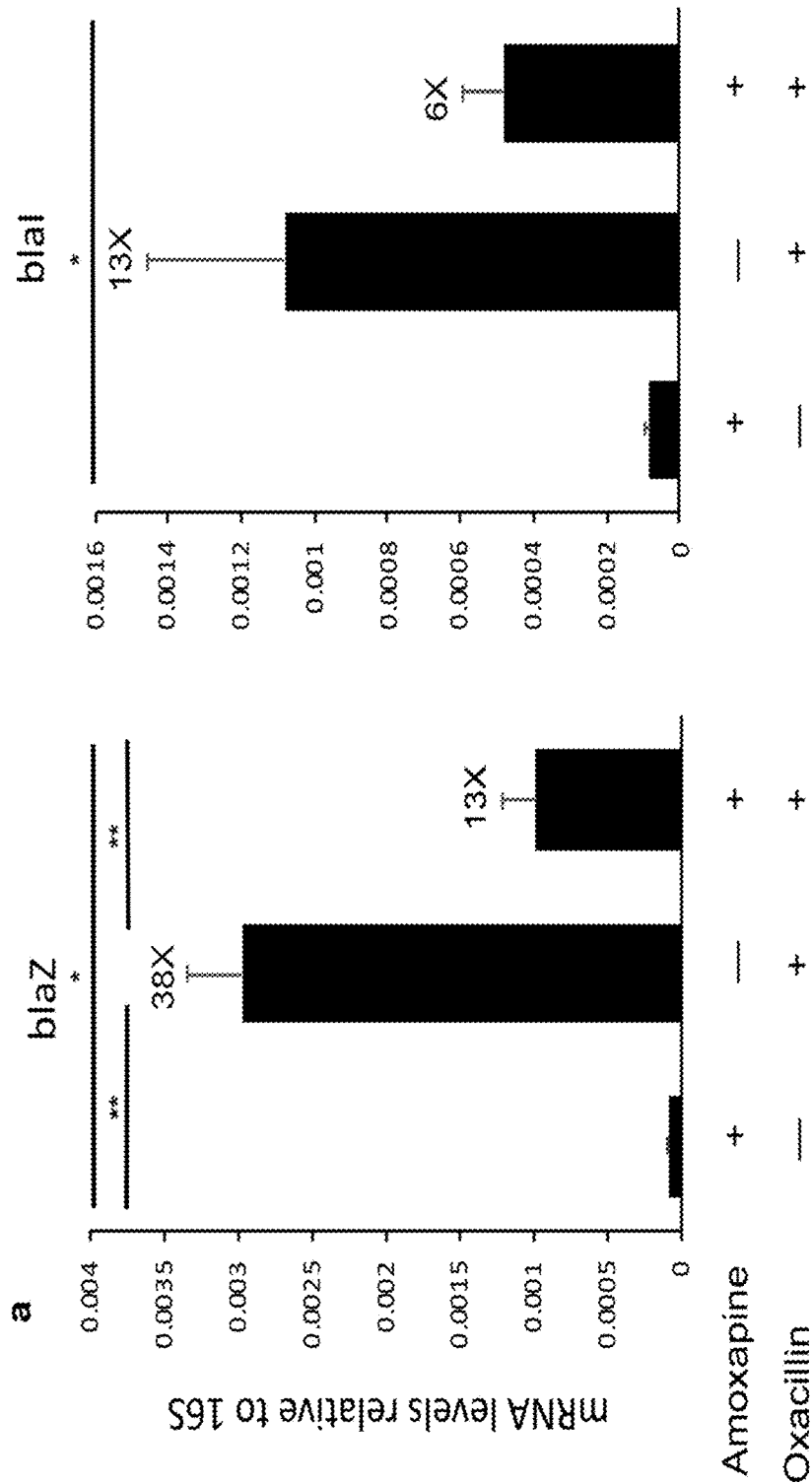
FIGS. 4A, 4B, 4C, 4D, and 4E are graphs of mRNA levels in the presence and absence of amoxapine.

It was hypothesized that amoxapine was affecting β-lactamase production by modulating transcription of the bla operon and preventing the upregulation of gene transcription in the presence of β-lactam antibiotics. To test this hypothesis, the effect of amoxapine on mRNA levels was analyzed by RT-qPCR. blaZ, the gene that encodes for the PC1 β-lactamase enzyme, and blaI, the gene that encodes for BlaI, the bla operon transcriptional repressor were quantified relative to 16S rRNA, which was the reference gene (see FIGS. 4A and 4B). As expected, treatment of cultures with oxacillin resulted in a statistically significant, 38-fold increase in blaZ (p=0.008). Co-treatment with amoxapine and oxacillin led to a 3.0-fold reduction in blaZ levels as compared to treatment with oxacillin alone (p=0.008). A 13-fold increase in blaI levels with oxacillin treatment, but a 2.2-fold reduction in blaI levels with co-treatment with amoxapine and oxacillin as compared to treatment with oxacillin alone was also observed. Although it seems counterintuitive that both blaI and blaZ would be upregulated upon treatment with oxacillin, all genes in the bla operon are under control of the same promoter and are co-transcribed in response to β-lactam treatment. See Blazquez, B. et al., "Regulation of the expression of the beta-lactam antibiotic-resistance determinants in methicillin-resistant *Staphylococcus aureus* (MRSA)," *Biochemistry* 2014, 53 (10), 1548; Staude, M. W. et al., "Investigation of signal transduction routes within the sensor/transducer protein BlaR1 of *Staphylococcus aureus*," *Biochemistry* 2015, 54 (8), 1600; Thumanu, K., et al., "Discrete steps in sensing of beta-lactam antibiotics by the BlaR1 protein of the methicillin-resistant *Staphylococcus aureus* bacterium," *Proc Natl Acad Sci USA* 2006, 103 (28), 10630, which are incorporated herein by reference in their entireties. Treatment with amoxapine alone showed no significant effect on mRNA levels as compared to the untreated control (data not shown).

Figures 4C, 4D:
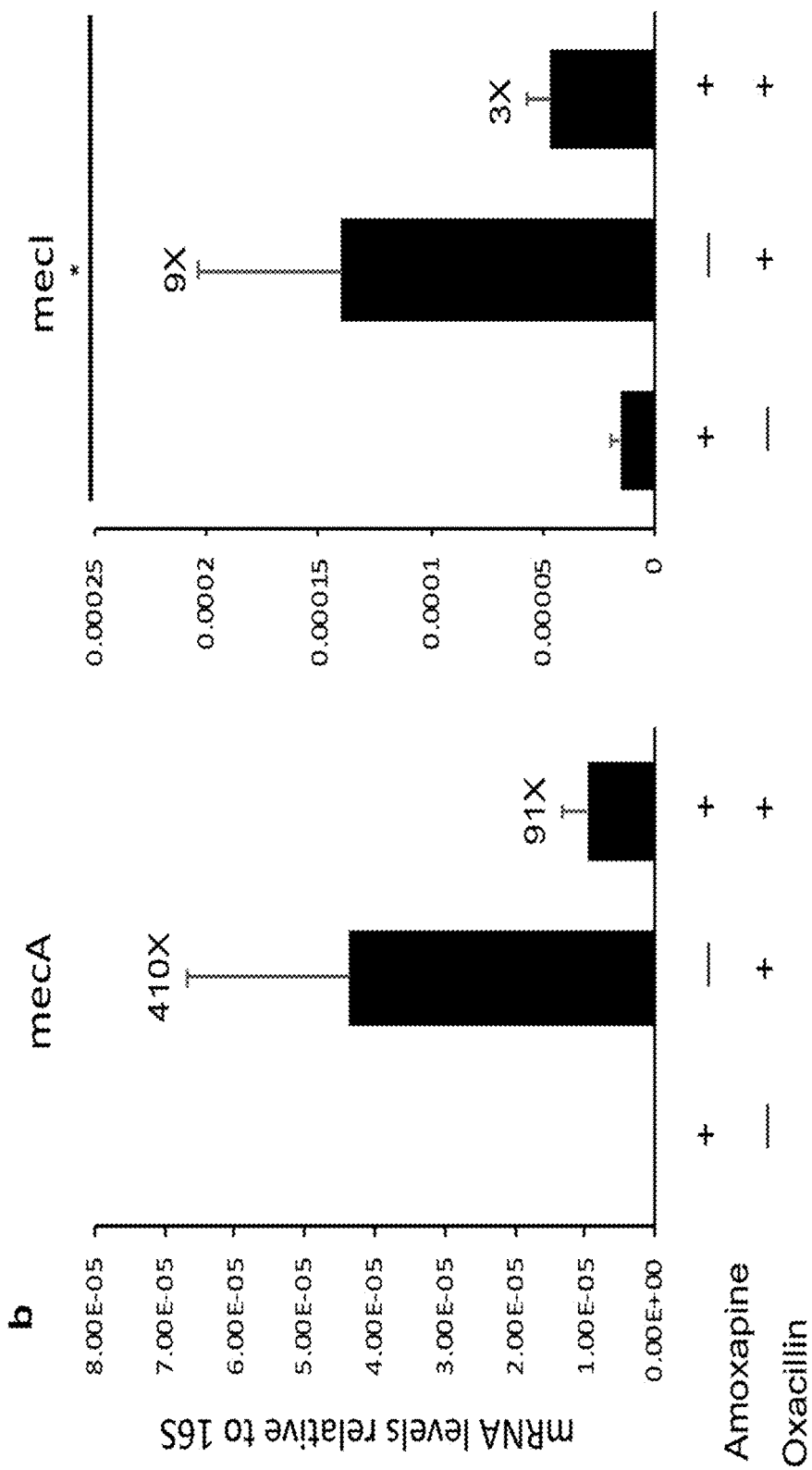
Figure 4E:
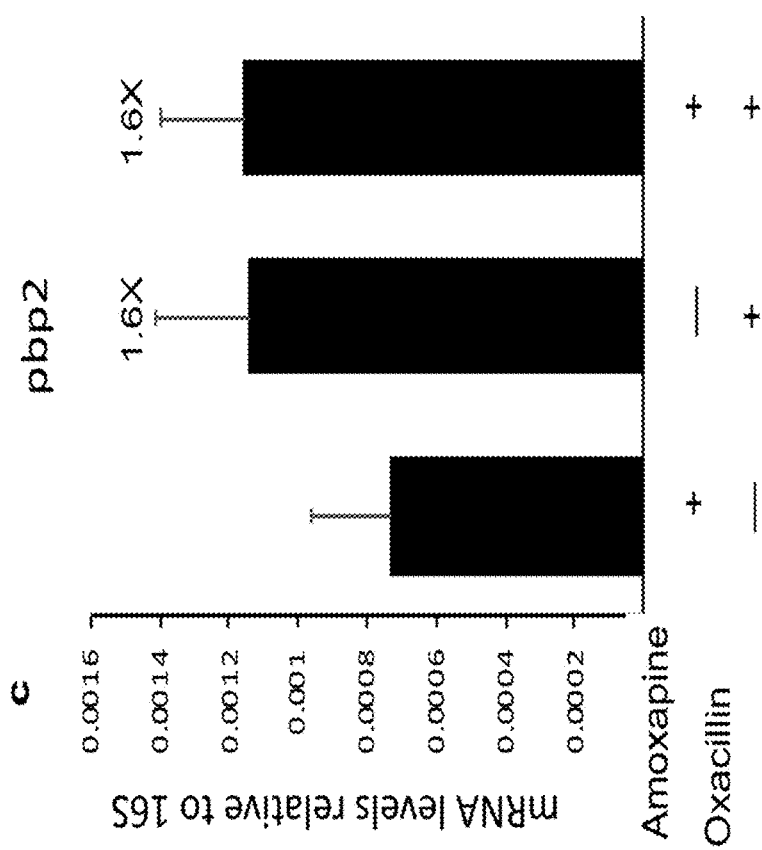

As the sensory and transcription regulation of both the bla and mec operons show marked similarity, mecA, the gene that encodes modified penicillin-binding protein PBP2a, and mecI, the gene that encodes for MecI, the mec operon transcriptional repressor were also analyzed (see FIGS. 4C and 4D). See Blazquez, B.; Llarrull, L. I.; Luque-Ortega, J. R.; Alfonso, C.; Boggess, B.; Mobashery, S. Regulation of the expression of the beta-lactam antibiotic-resistance determinants in methicillin-resistant *Staphylococcus aureus* (MRSA). *Biochemistry* 2014, 53 (10), 1548, which is incorporated herein by reference. Interestingly, co-treatment with amoxapine and oxacillin led to a 4.5-fold reduction in mecA mRNA levels and a 3.0-fold reduction in mecI mRNA levels as compared to treatment with oxacillin alone. Co-treatment with amoxapine and oxacillin had no significant effect on the mRNA levels of pbp2, the gene that encodes for penicillin-binding protein 2, as compared to treatment with oxacillin alone (see FIG. 4D). Together, these results suggest that amoxapine selectively dampens transcription of the β-lactam resistance genes blaZ and mecA in response to β-lactam exposure, thereby significantly impairing MRSA's ability to survive treatment with β-lactam antibiotics.

Although reduced mRNA levels could be attributed to increased mRNA degradation, the function of these operons points to a more likely decrease in transcription of the bla and mec operons. Additionally, other small molecule adjuvants with similar mechanisms of action have been described. FDA-approved phenothiazines, including thioridazine and chlorpromazine, similarly repotentiate MRSA to β-lactam antibiotics by inhibiting blaZ and mecA gene transcription in the presence of β-lactam antibiotics. See Thorsing, M.; Klitgaard, J. K.; Atilano, M. L.; Skov, M. N.; Kolmos, H. J.; Filipe, S. R.; Kallipolitis, B. H. Thioridazine induces major changes in global gene expression and cell wall composition in methicillin-resistant *Staphylococcus aureus* USA300. *PLoS One* 2013, 8 (5), e64518.

Example 2

Dibenzazepine and dibenzoxazepine derivatives based on compound I-5 were synthesized and analyzed for antibiotic adjuvant activity. Exemplary compounds tested are shown in FIG. 5. MICs of compounds II-2 through II-6 in *S. aureus* 43300 were all >200 μM. These iminodibenzyl derivatives were tested against *S. aureus* 43300 with oxacillin and the results are shown below in Table 6.

TABLE 6

MIC of oxacillin in combination with iminodibenzyl derivatives in S. aureus 43300 (MRSA)

| | +50 µM compound | |
|---|---|---|
| Compound | MIC (µg/mL) | Fold Reduction |
| — | 32 | — |
| I-5 | 2 | 16 |
| II-2 | 32 | 1 |
| II-3 | 16 | 2 |
| II-4 | 32 | 1 |
| II-5 | 8 | 4 |
| II-6 | 32 | 1 |

Further derivatives (II-7 through II-10, shown in FIG. 5) were also analyzed. MICs of compounds II-7 through II-10 in S. aureus 43300 were all >200 µM. These dibenzoxazepine derivatives were tested against S. aureus 43300 with oxacillin and the results are shown below in Table 7.

TABLE 7

MIC of oxacillin in combination with iminodibenzyl derivatives in S. aureus 43300 (MRSA)

| | +50 µM compound | |
|---|---|---|
| Compound | MIC (µg/mL) | Fold Reduction |
| — | 32 | — |
| II-7 | 32 | 1 |
| II-8 | 32 | 1 |
| II-9 | 32 | 1 |
| II-10 | 32 | 1 |

Example 3

Figure 6:
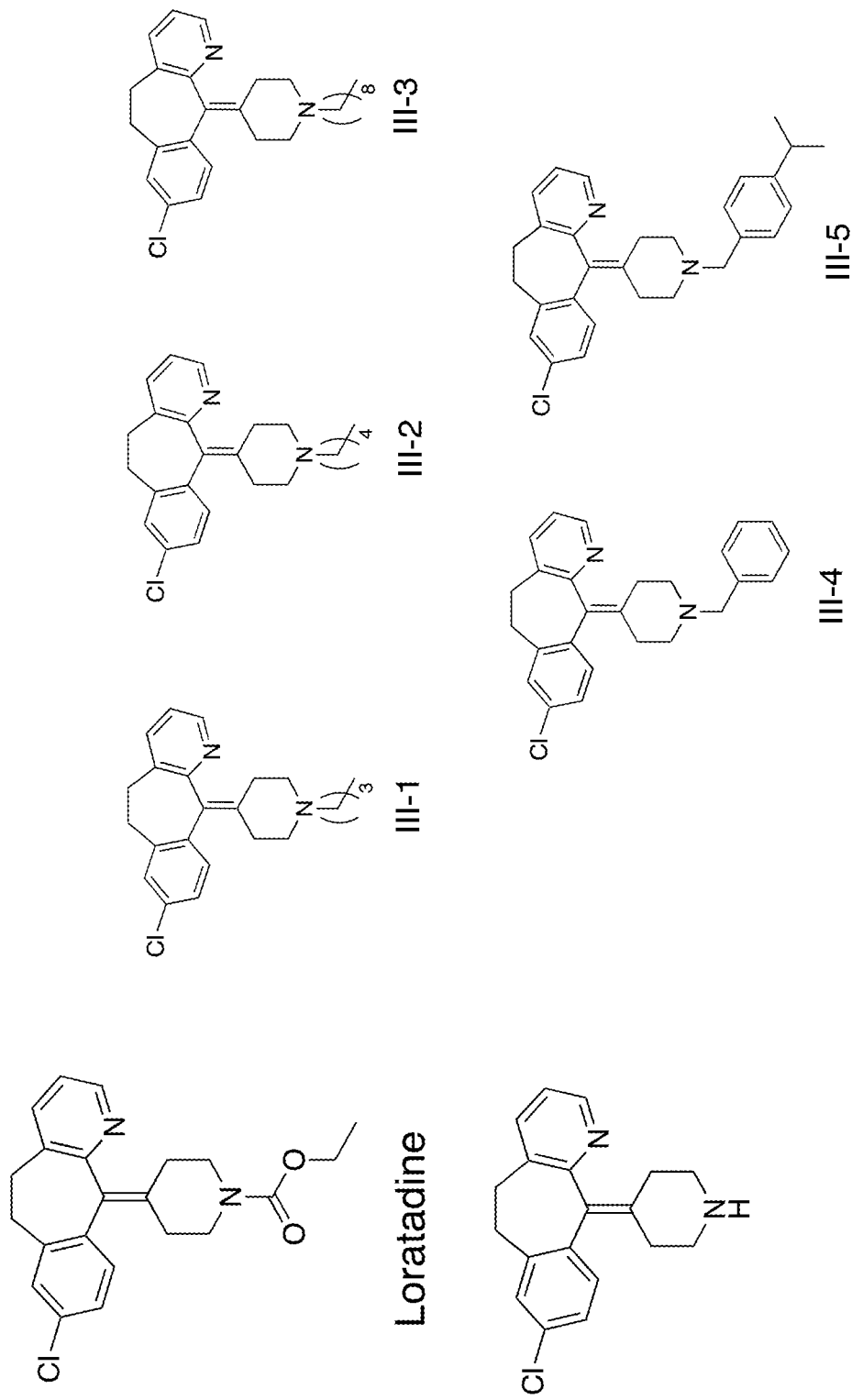
FIG. 6 shows various compounds evaluated for β-lactam antibiotic repotentiation in Example 3 provided herein.

Based on the structural similarities between the dibenzazepine scaffold and the benzocycloheptapyridine scaffold, loratadine and desloratadine, as well as derivatives of loratadine (as shown in FIG. 6) were analyzed for adjuvant activity in several strains of S. aureus. MICs for loratadine and desloratadine with various S. aureus strains are provided below in Table 8 and were all >200 µM, as shown.

TABLE 8

MICs of loratadine and desloratadine

| | MICs in CAMHB (µM) | |
|---|---|---|
| Bacterial Strain | Loratadine | Desloratadine |
| S. aureus ATCC 29213 | >200 | >200 |
| S. aureus* ATCC 43300 | >200 | >200 |
| S. aureus* USA100 | >200 | >200 |
| S. aureus* USA300 | >200 | >200 |
| S. aureus** NR-49120 | >200 | >200 |

*denotes methicillin resistant strain
**denotes vancomycin & methicillin resistant strain Table 9, provided herein below, provides MICs of oxacillin alone and in combination with loratadine and desloratadine. Loratadine showed potent potentiation of oxacillin across several medically relevant strains of antibiotic resistant S. aureus. USA100 is a common hospital-acquired strain of MRSA that displays high levels of resistance to β-lactam antibiotics and is the strain that most commonly evolves into vancomycin-resistant S. aureus. As noted previously, USA300 is a community-acquired strain of MRSA that is common in the United States and Europe. NR-49120 is a vancomycin-resistant strain of S. aureus.

TABLE 9

MICs of oxacillin alone and in combination with loratadine and desloratadine

| | | +Loratadine (50 µM) | | +Desloratadine (50 µM) | |
|---|---|---|---|---|---|
| Bacterial Strain | Oxacillin MIC (µg ml$^{-1}$) | Oxacillin MIC (µg ml$^{-1}$) | Fold Reduction | Oxacillin MIC (µg ml$^{-1}$) | Fold Reduction |
| S. aureus ATCC 43300* | 32 | 1 | 32 | 16 | 2 |
| S. aureus USA100* | 256 | 0.5 | 512 | 256 | 1 |
| S. aureus USA300* | 32 | 0.5 | 64 | 32 | 1 |
| S. aureus NR-49120** | 128 | 16 | 8 | 128 | 1 |

*denotes methicillin resistant strain
denotes vancomycin & methicillin resistant strain As loratadine showed markedly increased activity over desloratadine, synthetic derivatives of loratadine were also investigated for adjuvant activity. Loratadine derivatives III-1 through III-5 shown in FIG. 6** were all tested against S. aureus 43300 and all had MICs of >200 µM. Table 10, below, provides MICs of oxacillin in combination with these loratadine derivatives against S. aureus 43300 (MRSA).

TABLE 10

MIC of oxacillin in combination with loratadine derivatives in S. aureus 43300 (MRSA)

| | +50 µM compound | |
|---|---|---|
| Compound | MIC (µg/mL) | Fold Reduction |
| — | 32 | — |
| III-1 | 32 | 1 |
| III-2 | 1 | 32 |
| III-3 | 32 | 1 |
| III-4 | 32 | 1 |
| III-5 | 2 | 16 |

Cell wall active antibiotics were next analyzed alone and in combination with loratadine and desloratadine, with the results provided below in Table 11. Loratadine potentiates β-lactam and cephalosporin antibiotics in all strains tested. Importantly, loratadine is also able to potentiate the antibiotic vancomycin in a strain with vancomycin resistance.

TABLE 11

MIC of cell wall active antibiotics alone and in combination with loratadine

| | MRSA 43300* | | | | | | MRSA USA100* | | | | |
|---|---|---|---|---|---|---|---|---|---|---|---|
| | | +Loratadine (25/50 µM) | | | | | | +Loratadine (25/50 µM) | | | |
| Antibiotic | MIC (µg ml$^{-1}$) | MIC (µg ml$^{-1}$) | | Fold Reduction | | | MIC (µg ml$^{-1}$) | MIC (µg ml$^{-1}$) | | Fold Reduction | |
| Penicillin G | 16 | 4 | | 2 | 4 | 8 | 32 | 16 | | 1 | 2 | 32 |
| Ampicillin | 16 | 16/8 | | 1/2 | 1/2 | 4 | 32 | 16 | | 1/2 | 2 | 32/16 |
| Cefazolin | 64 | 16 | | 1 | 4 | 64 | 256 | 128 | | 1 | 2 | 256 |
| Oxacillin | 32 | 4 | | 1 | 8 | 32 | 256 | 128 | | 0.25 | 2 | 1024 |
| Vancomycin | 1 | 1 | | 1 | 1 | 1 | 2 | 2 | | 2 | 1 | 1 |

| | MRSA USA300* | | | | | | VRSA NR-49120** | | | | |
|---|---|---|---|---|---|---|---|---|---|---|---|
| | | +Loratadine (25/50 µM) | | | | | | +Loratadine (25/50 µM) | | | |
| Antibiotic | MIC (µg ml$^{-1}$) | MIC (µg ml$^{-1}$) | | Fold Reduction | | | MIC (µg ml$^{-1}$) | MIC (µg ml$^{-1}$) | | Fold Reduction | |
| Penicillin G | 4/8 | 4 | | 0.125/0.25 | 1/2 | 32 | 16 | 8 | | 2 | 2 | 8 |
| Ampicillin | 8 | 8 | | 0.5 | 1 | 16 | 16 | 16 | | 4 | 1 | 4 |
| Cefazolin | 32 | 4 | | 1 | 8 | 32 | 128 | 32 | | 8 | 4 | 16 |
| Oxacillin | 32 | 2 | | 0.5 | 16 | 64 | 128 | 64 | | 16 | 2 | 8 |
| Vancomycin | 1 | 1 | | 1 | 1 | 1 | 1024 | 512 | | 128 | 2 | 8 |

Figure 7:
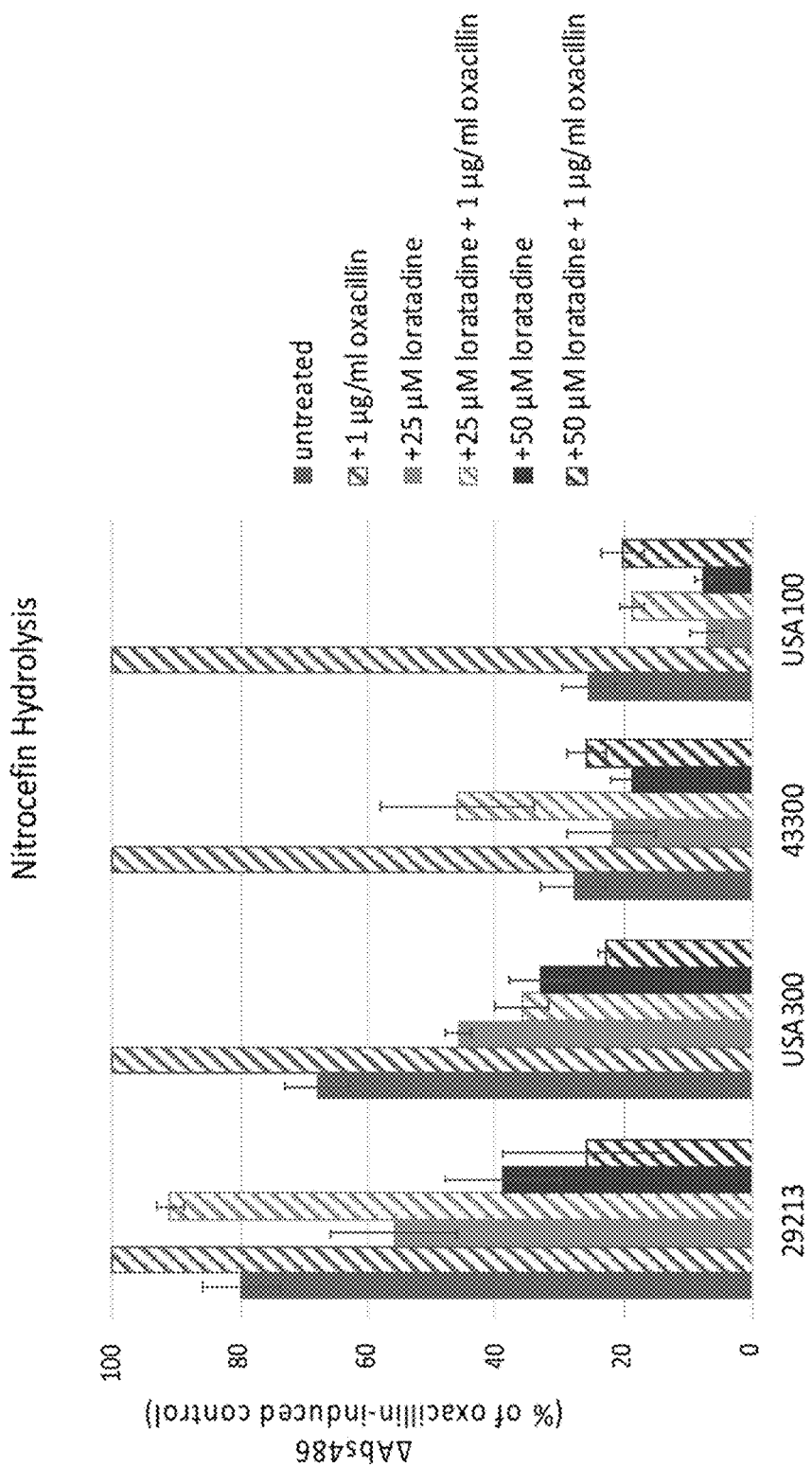
FIG. 7 is a graph providing data on nitrocefin hydrolysis assays conducted with oxacillin and loratadine.

*denotes methicillin resistant strain
**denotes vancomycin & methicillin resistant strain A nitrocefin hydrolysis assay was conducted with oxacillin and loratadine as described above in Example 1. Briefly, cultures of *S. aureus* were incubated with the indicated combination of oxacillin and loratadine for 30 minutes before exposure to nitrocefin, a chromogenic β-lactamase substrate. Absorbance at 486 nm was monitored for 2 hours for strains 29213, USA300, and 43300 and for 30 minutes for strain USA100. The change in absorbance at 486 nm is expressed as a percentage of the oxacillin-induced control. The mean of 3 independent biological replicates, each performed with 4 technical replicates, is shown. The results are shown in FIG. 7, where error bars represent standard deviation.

Example 4

Figure 8:
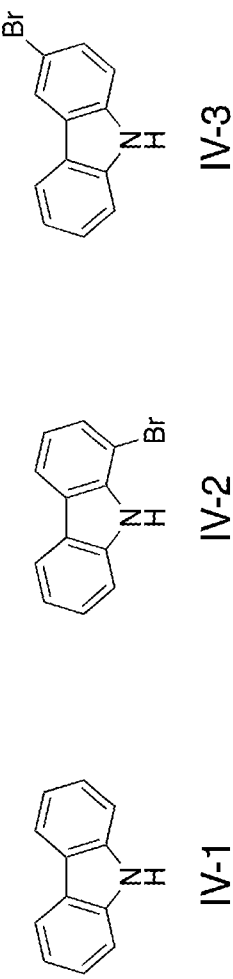
FIG. 8 shows various compounds evaluated for β-lactam antibiotic repotentiation in Example 4 provided herein.
Figure 8:
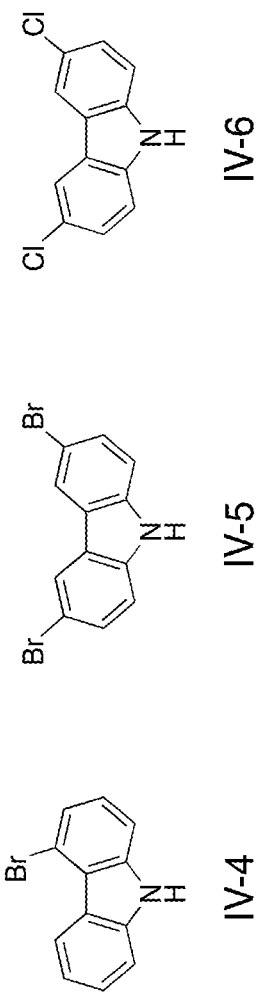

Various carbazoles (as shown in FIG. 8) were analyzed for adjuvant activity in *S. aureus*. MICs for these carbazoles with various bacterial strains are provided below in Table 12.

TABLE 12

MICs of carbazole derivatives in *S. aureus* strains

| Compound | MIC (µM) in S. aureus 43300 | MIC (µM) in S. aureus USA100 | MIC (µM) in S. aureus USA300 |
|---|---|---|---|
| IV-1 | >200 | >200 | >200 |
| IV-2 | >200 | >200 | >200 |
| IV-3 | >200 | >200 | >200 |
| IV-4 | 200 | 100 | 100 |
| IV-5 | >200 | >200 | >200 |
| IV-6 | >200 | >200 | >200 |

Tables providing MIC values of oxacillin in combination with carbazole derivatives in various *S. aureus* strains are provided in Tables 13-15. The carbazoles display adjuvant activity across multiple strains of medically relevant *S. aureus*.

TABLE 13

MIC of oxacillin in combination with carbazole derivatives in *S. aureus* 43300 (MRSA)

| | +50 µM compound | |
|---|---|---|
| Compound | MIC (µg/mL) | Fold Reduction |
| — | 32 | — |
| IV-1 | 32 | 1 |
| IV-2 | 4 | 8 |
| IV-3 | 16 | 2 |
| IV-4 | 32 | 1 |
| IV-5 | 8/4 | 4/8 |
| IV-6 | 1 | 32 |

TABLE 14

MIC of oxacillin in combination with carbazole derivatives in *S. aureus* USA100 (MRSA)

| | +50 µM compound | |
|---|---|---|
| Compound | MIC (µg/mL) | Fold Reduction |
| — | 512 | — |
| IV-1 | 512 | 1 |
| IV-2 | 8 | 64 |
| IV-3 | 512 | 1 |
| IV-4 | 4 | 128 |
| IV-5 | 4 | 128 |
| IV-6 | 0.5/0.25 | 1024/2048 |

TABLE 15

MIC of oxacillin in combination with carbazole derivatives in S. aureus USA300 (MRSA)

| | +50 µM compound | |
|---|---|---|
| Compound | MIC (µg/mL) | Fold Reduction |
| — | 64 | — |
| IV-1 | 64 | 1 |
| IV-2 | 16/8 | 4/8 |
| IV-3 | 64 | 1 |
| IV-4 | 2 | 32 |
| IV-5 | 32 | 2 |
| IV-6 | 16/8 | 4/8 |

Example 5

Figure 9:
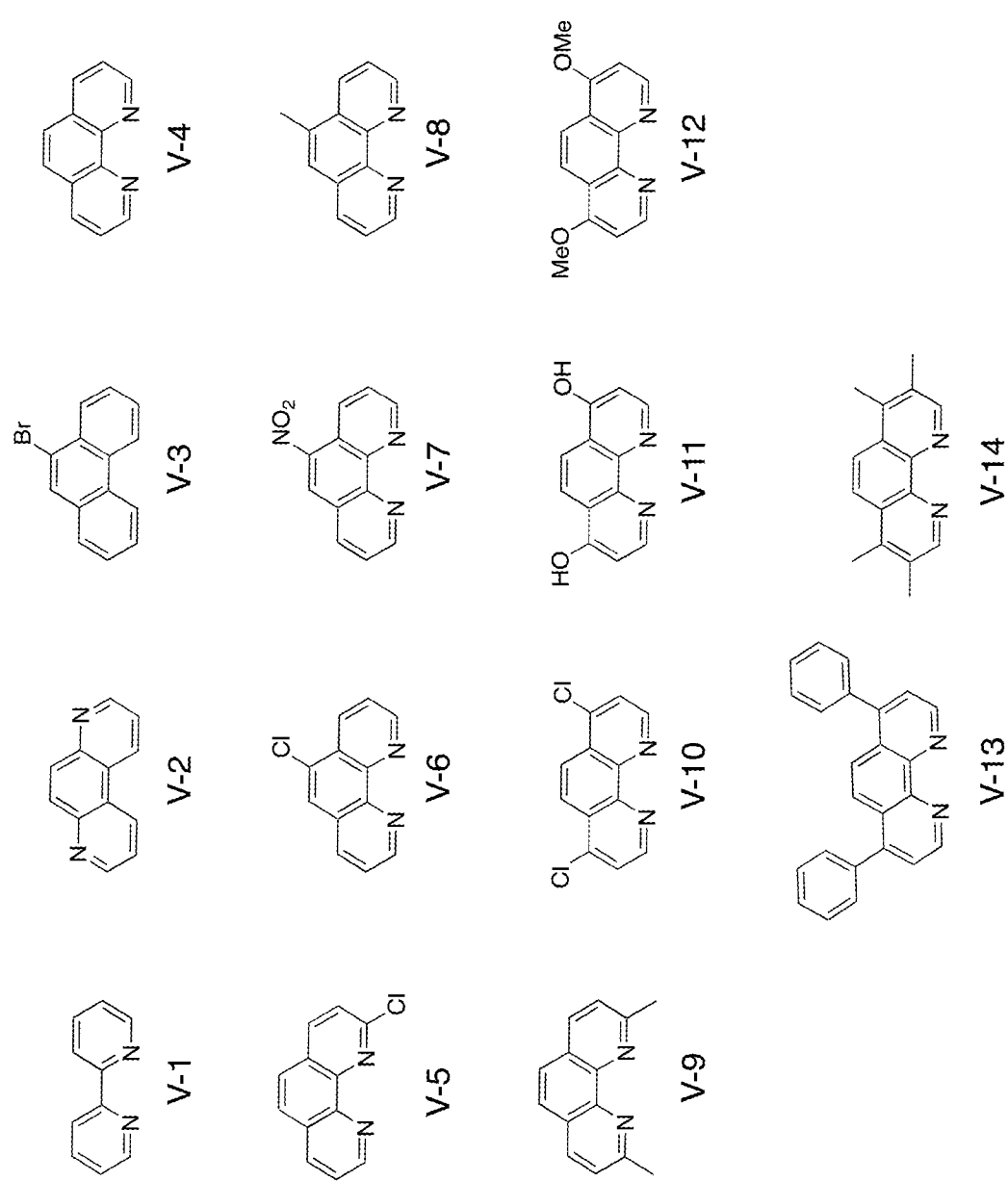
FIG. 9 shows various compounds evaluated for β-lactam antibiotic repotentiation in Example 5 provided herein.

Certain phenanthrolines (as shown in FIG. 9) were analyzed. MICs for these phenanthrolines are provided below in Table 16 and MICs of oxacillin in combination with these compounds are provided in Table 17.

TABLE 16

MICs of phenanthrolines and phenanthroline derivatives in S. aureus 43300 (MRSA)

| Compound | MIC (µM) |
|---|---|
| V-1 | >2000 |
| V-2 | 1000 |
| V-3 | >250 |
| V-4 | 125 |
| V-5 | 1000 |
| V-6 | 125 |
| V-7 | 31.25 |
| V-8 | 125 |
| V-9 | 125 |
| V-10 | >500 |
| V-11 | 250 |
| V-12 | 31.25 |
| V-13 | 6.25 |
| V-14 | 3.125 |

TABLE 17

MIC of oxacillin in combination with phenanthrolines and phenanthroline derivatives in S. aureus 43300 (MRSA)

| Compound | Compound Concentration (µM) | Oxacillin MIC (µg/mL) | Fold Reduction |
|---|---|---|---|
| — | — | 32 | — |
| V-1 | 100 | 32 | 1 |
| V-2 | 100 | 32 | 1 |
| V-3 | 75 | 8 | 4 |
| V-4 | 31.25 | 8 | 4 |
| V-5 | 100 | 32 | 1 |
| V-6 | 31.25 | 4 | 8 |
| V-7 | 7.8125 | 16 | 2 |
| V-8 | 31.25 | 2 | 16 |
| V-9 | 31.25 | 32 | 1 |
| V-10 | 75 | 32 | 1 |
| V-11 | 62.5 | 32 | 1 |
| V-12 | 7.8 | 4 | 8 |
| V-13 | 1.56 | 16 | 2 |
| V-14 | 0.78 | 32 | 1 |

Example 7

Antibiotic resistance and biofilm formation share similar regulatory mechanisms. The biofilm inhibition activity of several of the above compounds was analyzed to determine if these compounds also inhibited biofilm formation in S. aureus. Biofilm inhibition was first assessed in S. aureus 43300, a methicillin-resistant strain (see Table 18). As described in Materials and Methods, a standard crystal violet assay was used to assess biofilm inhibition by the tested compounds. The $IC_{50}$ is described as the compound concentration required to inhibit 50% of biofilm formation. The standard deviation is calculated from at least 3 independent experiments.

TABLE 18

Biofilm Inhibition in MRSA 43300

| Compound | $IC_{50}$ (µM) | Std. Deviation |
|---|---|---|
| Amoxapine | 333.1 | ±27.4 |
| I-5 | 18.65 | ±5.64 |
| Loratadine | 11.49 | ±2.54 |
| Desloratadine | >200 | — |
| IV-6 | 10.21 | ±4.39 |
| V-6 | 184.28 | ±11.91 |

The biofilm inhibition activity of loratadine was further explored in other strains of S. aureus. The results of this study can be seen in Table 19. Loratadine was capable of inhibiting biofilm formation in all tested strains of S. aureus, including methicillin-resistant and vancomycin-resistant strains. Among S. aureus strains, the most potent biofilm inhibition was observed in the hospital-acquired MRSA strain 43300 with an $IC_{50}$ of 11.4 µM.

TABLE 19

Inhibition of S. aureus biofilms by loratadine

| Bacterial Strain | Loratadine $IC_{50}$ (µM) |
|---|---|
| S. aureus 29213 | 25.88 ± 2.36 |
| S. aureus 43300* | 11.49 ± 2.54 |
| S. aureus USA100* | 22.18 ± 6.51 |
| S. aureus USA300* | 32.79 ± 5.90 |
| S. aureus NR-49120** | 59.90 ± 1.29 |
| S. aureus NR-50109** | 19.11 ± 2.87 |

*denotes methicillin-resistant strain
**denotes methicillin and vancomycin resistant strain Loratadine was also tested for the ability to disperse pre-formed biofilms. Biofilm dispersion is reported as an $EC_{50}$, which is defined as the concentration of compound required to disperse 50% of the preformed biofilm. Loratadine exhibited modest biofilm dispersion of hospital-acquired MRSA strain USA100 biofilms with an $EC_{50}$ of 121.47 µM (see Table 20).

TABLE 20

Dispersion of S. aureus biofilms by loratadine

| Bacterial Strain | Loratadine $EC_{50}$ (µM) |
|---|---|
| S. aureus 29213 | >200 |
| S. aureus 43300* | >200 |
| S. aureus USA100* | 121.47 ± 22.16 |
| S. aureus USA300* | >200 |

*denotes methicillin-resistant strain
**denotes methicillin and vancomycin resistant strain

Example 8

Antibiotic potentiation in *S. epidermidis* was also investigated. Several of the compounds identified above show modest oxacillin potentiation in methicillin-resistant *S. epidermidis* (see Table 21).

TABLE 21

MIC of oxacillin in combination with various compounds in *S. epidermidis* 49461

| Compound | Compound Concentration (μM) | Oxacillin MIC (μg/mL) | Fold Reduction |
|---|---|---|---|
| None | — | 16 | — |
| Amoxapine | 75 | 4 | 4 |
| Clozapine | 75 | 16 | 1 |
| Loxapine | 75 | 8 | 2 |
| Clothiapine | 75 | 4 | 4 |
| Loratadine | 50 | 16 | 1 |

Biofilm inhibition activity of many of the compounds mentioned previously was studied in *S. epidermidis* (See Table 22). Several compounds displayed excellent biofilm inhibition potential in *S. epidermidis*. Of the FDA-approved compounds, loratadine displays the most potent biofilm inhibition with an $IC_{50}$ of 25.09±3.65 μM. Several phenanthroline derivatives also showed potent inhibition activity. In particular, compound V-9 inhibits more than 50% of biofilm formation at concentrations less than 5 μM.

TABLE 22

Inhibition of biofilm formation in *S. epidermidis* ATCC 49461

| Compound | $IC_{50}$ (μM) | Std. Deviation |
|---|---|---|
| Amoxapine | 155.53 | ±21.98 |
| Clozapine | 149.10 | ±5.86 |
| Loxapine | 270.38 | ±5.46 |
| Clothiapine | 119.31 | ±25.36 |
| Loratadine | 25.09 | ±3.65 |
| III-1 | >80 | — |
| III-2 | 26.90 | ±1.48 |
| III-3 | >80 | — |
| III-4 | >50 | — |
| III-5 | 62.21 | ±11.62 |
| V-1 | >100 | — |
| V-2 | 84.58 | ±44.65 |
| V-3 | >100 | — |
| V-4 | 51.82 | ±1.70 |
| V-5 | 38.48 | ±4.79 |
| V-6 | 57.07 | ±5.49 |
| V-7 | >100 | — |
| V-8 | 78.92 | ±1.05 |
| V-9 | <5 | — |
| V-10 | 27.26 | ±14.86 |
| V-11 | >100 | — |
| V-12 | >100 | — |
| V-13 | >100 | — |
| V-14 | >100 | — |

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed herein is:

1. A method for treating a bacterial infection in a patient caused by *Staphylococcus aureus*, comprising administering an antibiotic and an adjuvant compound to the patient, wherein the adjuvant compound has a structure according to the formula;

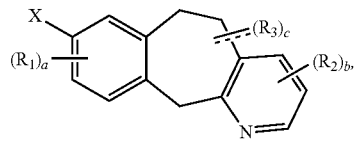

wherein:
X is a halogen substituent selected from Cl, F, Br, and I;
$R_1$ and $R_2$ are independently selected from halo; optionally substituted heteroalkyl, optionally substituted C2-4 alkenyl, optionally substituted C2-4 alkynyl; hydroxyl; amino; amido; carboxylate; carboxamido; carbamate; carbonate; urea; acetate; alkylamino; arylamino; acyl; C1-10 alkoxy; aryl; aralkyl, alkaryl, aryloxy; nitro; azido; cyano; thio; alkylthio; sulfonate; sulfide; sulfinyl; sulfo; sulfate; sulfoxide; sulfamide; sulfonamide; phosphonic acid; phosphate; and/or phosphonate;
$R_3$ is substituted piperazine;
a is an integer of 0 to 4;
b is an integer of 0 to 5;
c is an integer of 0 to 3; and
the dashed lines represent optional double bonds,
wherein the antibiotic and the adjuvant compound are formulated in a composition to be administered in a manner other than nasal administration, and
wherein the composition comprises no further active agents in addition to the antibiotic and the adjuvant compound.

2. The method of claim 1, wherein the adjuvant compound is loratadine.

3. The method of claim 1, wherein the antibiotic is a β-lactam antibiotic.

4. The method of claim 1, wherein the antibiotic is an aminoglycoside antibiotic.

5. The method of claim 3, wherein the β-lactam antibiotic is a penicillin or a cephalosporin antibiotic.

6. The method of claim 3, wherein the β-lactam antibiotic is selected from the group consisting of ampicillin, cefazolin, oxacillin, penicillin G, and combinations thereof.

7. The method of claim 4, wherein the antibiotic is vancomycin.

8. The method of claim 1, wherein the antibiotic and the adjuvant compound are administered simultaneously by administration in the same composition or in separate compositions.

9. The method of claim 1, wherein the antibiotic and the adjuvant compound are administered at different times.

10. The method of claim 1, wherein the antibiotic and the adjuvant compound are administered orally, parenterally, or topically.

11. The method of claim 1, wherein the antibiotic is administered in an amount less than its minimum inhibitory concentration when used alone.

12. The method of claim 1, wherein the *Staphylococcus aureus* is Methicillin-resistant *Staphylococcus aureus* (MRSA).

13. The method of claim 1, wherein the dashed line adjacent to $R_3$ is a double bond.

14. The method of claim 1, wherein the optionally substituted piperazine is substituted with alkyl or alkaryl.
15. The method of claim 1, wherein the adjuvant compound is selected from the group consisting of:
III-1
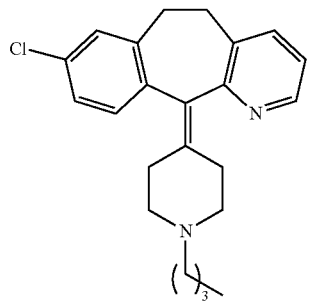
III-2
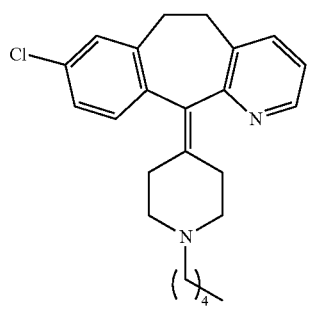
III-3
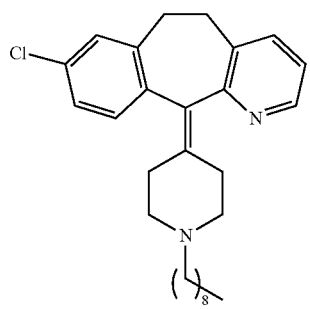
III-4
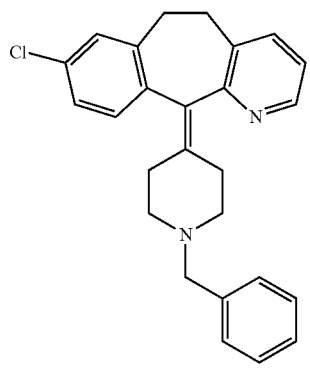
-continued
III-5
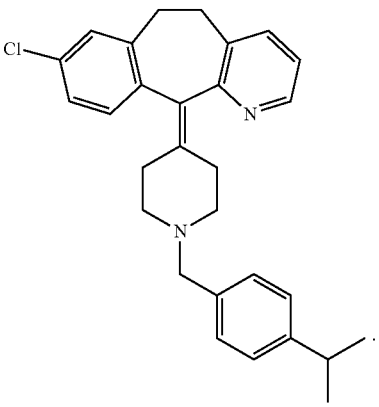
16. The method of claim 1, wherein the adjuvant compound is selected from the group consisting of:
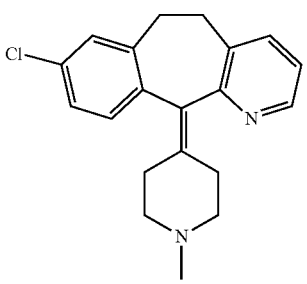
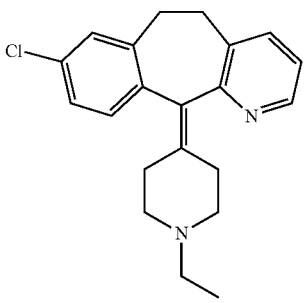
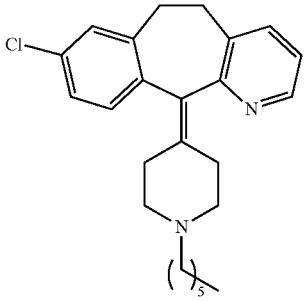

-continued

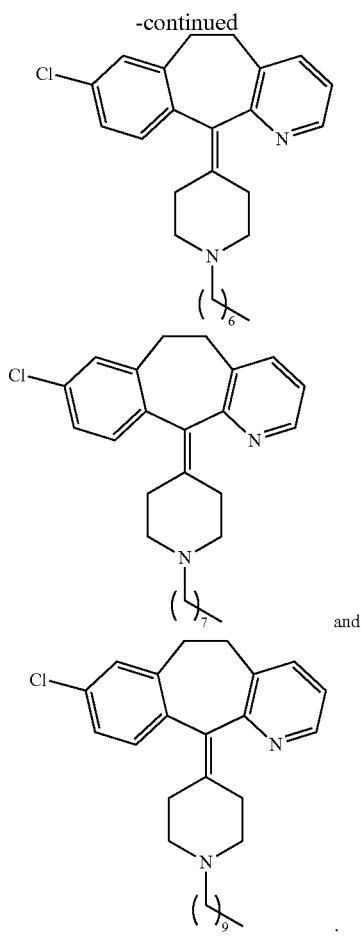

17. The method of claim 1, wherein the adjuvant compound is administered in an amount of less than or equal to about 25% of its minimum inhibitory concentration ("MIC").

18. The method of claim 2, wherein the adjuvant compound is administered in an amount of less than or equal to about 25% of its minimum inhibitory concentration ("MIC").

19. A method for treating a bacterial infection in a patient caused by *Staphylococcus aureus*, comprising administering an antibiotic and an adjuvant compound to the patient,
wherein the antibiotic is β-lactam antibiotic; and
wherein the adjuvant compound has a structure according to the formula;

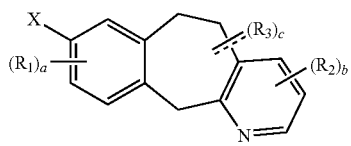

wherein:
X is a halogen substituent selected from Cl, F, Br, and I;
$R_1$ and $R_2$ are independently selected from halo; optionally substituted heteroalkyl, optionally substituted C2-4 alkenyl, optionally substituted C2-4 alkynyl; hydroxyl; amino; amido; carboxylate; carboxamido; carbamate; carbonate; urea; acetate; alkylamino; arylamino; acyl; C1-10 alkoxy; aryl; aralkyl, alkaryl, aryloxy; nitro; azido; cyano; thio; alkylthio; sulfonate; sulfide; sulfinyl; sulfo; sulfate; sulfoxide; sulfamide; sulfonamide; phosphonic acid; phosphate; and/or phosphonate;
$R_3$ is substituted piperazine;
a is an integer of 0 to 4;
b is an integer of 0 to 5;
c is an integer of 0 to 3; and
the dashed lines represent optional double bonds,
wherein the antibiotic and the adjuvant compound are formulated in a composition to be administered in a manner other than nasal administration, and
wherein the composition comprises no further active agents in addition to the antibiotic and the adjuvant compound.

20. A method for treating a bacterial infection in a patient caused by *Staphylococcus aureus*, comprising administering an antibiotic and an adjuvant compound to the patient,
wherein the adjuvant compound has a structure according to the formula;

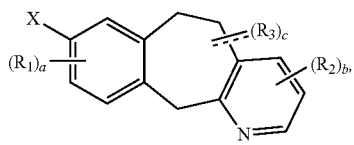

wherein:
X is a halogen substituent selected from Cl, F, Br, and I;
$R_1$ and $R_2$ are independently selected from halo; optionally substituted heteroalkyl, optionally substituted C2-4 alkenyl, optionally substituted C2-4 alkynyl; hydroxyl; amino; amido; carboxylate; carboxamido; carbamate; carbonate; urea; acetate; alkylamino; arylamino; acyl; C1-10 alkoxy; aryl; aralkyl, alkaryl, aryloxy; nitro; azido; cyano; thio; alkylthio; sulfonate; sulfide; sulfinyl; sulfo; sulfate; sulfoxide; sulfamide; sulfonamide; phosphonic acid; phosphate; and/or phosphonate;
$R_3$ is substituted piperazine;
a is an integer of 0 to 4;
b is an integer of 0 to 5;
c is an integer of 0 to 3; and
the dashed lines represent optional double bonds,
wherein the composition comprises no further active agents in addition to the antibiotic and the adjuvant compound.

* * * * *